US012521112B2

(12) United States Patent
Schings et al.

(10) Patent No.: US 12,521,112 B2
(45) Date of Patent: Jan. 13, 2026

(54) STAPLE AND STAPLE-FORMING POCKET ARRANGEMENTS FOR SURGICAL STAPLERS

(71) Applicant: Cilag GmbH International, Zug (CH)

(72) Inventors: Brian D. Schings, Maineville, OH (US); Andréas N. Ward, Cincinnati, OH (US)

(73) Assignee: CILAG GMBH INTERNATIONAL, Zug (CH)

(*) Notice: Subject to any disclaimer, the term of this patent is extended or adjusted under 35 U.S.C. 154(b) by 0 days.

(21) Appl. No.: 18/639,114

(22) Filed: Apr. 18, 2024

(65) Prior Publication Data

US 2024/0260961 A1 Aug. 8, 2024

Related U.S. Application Data

(63) Continuation of application No. 17/485,586, filed on Sep. 27, 2021, now Pat. No. 12,004,744.

(51) Int. Cl.
*A61B 17/072* (2006.01)

(52) U.S. Cl.
CPC ................... *A61B 17/07207* (2013.01); *A61B 2017/07264* (2013.01); *A61B 2017/07271* (2013.01); *A61B 2017/07285* (2013.01)

(58) Field of Classification Search
CPC .... A61B 17/07207; A61B 2017/07264; A61B 2017/07271; A61B 2017/07285
USPC ................................ 227/180.1, 175.1–182.1
See application file for complete search history.

(56) References Cited

U.S. PATENT DOCUMENTS

| | | | | |
|---|---|---|---|---|
| 2,277,931 | A | 3/1942 | Moe | |
| 4,047,654 | A | 9/1977 | Alvarado | |
| 4,407,286 | A | 10/1983 | Noiles et al. | |
| 4,505,273 | A | 3/1985 | Braun et al. | |
| 4,632,290 | A * | 12/1986 | Green | A61B 17/072 227/19 |
| 4,669,647 | A | 6/1987 | Storace | |
| 4,848,328 | A | 7/1989 | Laboureau et al. | |
| 4,874,122 | A | 10/1989 | Froelich et al. | |
| 4,899,745 | A | 2/1990 | Laboureau et al. | |
| 5,292,053 | A | 3/1994 | Bilotti et al. | |

(Continued)

FOREIGN PATENT DOCUMENTS

| | | | |
|---|---|---|---|
| CN | 202982106 | U | 6/2013 |
| EP | 0072754 | A2 | 2/1983 |

(Continued)

OTHER PUBLICATIONS

European Examination Report, dated Feb. 26, 2025 for Application No. EP 22786478.2, 14 pgs.

(Continued)

*Primary Examiner* — Dariush Seif
(74) *Attorney, Agent, or Firm* — FROST BROWN TODD LLP

(57) ABSTRACT

An apparatus includes a stapling assembly and an anvil. The stapling assembly includes first and second staples. Each of the first and second staples include first legs. The anvil together with the stapling assembly is configured to clamp tissue of a patient. The anvil includes a first staple forming (Continued)

pocket that is configured to transition the first legs of the first and second staples from a non-deformed state to a deformed state with the same firing stroke.

20 Claims, 25 Drawing Sheets

(56) References Cited

U.S. PATENT DOCUMENTS

| | | | | | |
|---|---|---|---|---|---|
| 5,333,773 | A | | 8/1994 | Main et al. | |
| 5,342,396 | A | | 8/1994 | Cook | |
| 5,350,104 | A | | 9/1994 | Main et al. | |
| 5,350,400 | A | * | 9/1994 | Esposito | A61B 17/0644 411/457 |
| 5,389,098 | A | | 2/1995 | Tsuruta et al. | |
| 5,425,489 | A | | 6/1995 | Shichman et al. | |
| 5,484,451 | A | * | 1/1996 | Akopov | A61B 17/04 227/176.1 |
| 5,533,661 | A | | 7/1996 | Main et al. | |
| 5,571,285 | A | | 11/1996 | Chow et al. | |
| 5,725,554 | A | | 3/1998 | Simon et al. | |
| 5,732,872 | A | | 3/1998 | Bolduc et al. | |
| 5,833,695 | A | * | 11/1998 | Yoon | A61B 17/07207 227/176.1 |
| 6,352,541 | B1 | | 3/2002 | Kienzle et al. | |
| 6,425,903 | B1 | | 7/2002 | Voegele | |
| 6,616,686 | B2 | | 9/2003 | Coleman et al. | |
| 6,767,356 | B2 | | 7/2004 | Kanner et al. | |
| 6,915,937 | B2 | | 7/2005 | Lat et al. | |
| 7,056,330 | B2 | | 6/2006 | Gayton | |
| 7,404,508 | B2 | | 7/2008 | Smith et al. | |
| 7,422,138 | B2 | | 9/2008 | Bilotti et al. | |
| 7,434,715 | B2 | | 10/2008 | Shelton, IV et al. | |
| 7,721,930 | B2 | | 5/2010 | McKenna et al. | |
| 7,824,426 | B2 | * | 11/2010 | Racenet | A61B 17/068 227/175.1 |
| 7,926,691 | B2 | * | 4/2011 | Viola | A61B 17/068 227/175.1 |
| 8,143,870 | B2 | | 3/2012 | Ng et al. | |
| 8,210,411 | B2 | | 7/2012 | Yates et al. | |
| 8,328,063 | B2 | | 12/2012 | Milliman et al. | |
| 8,408,439 | B2 | | 4/2013 | Huang et al. | |
| 8,453,914 | B2 | | 6/2013 | Laurent et al. | |
| 8,496,155 | B2 | * | 7/2013 | Knodel | A61B 17/07207 227/176.1 |
| 8,590,762 | B2 | | 11/2013 | Hess et al. | |
| 8,613,384 | B2 | | 12/2013 | Pastorelli et al. | |
| 8,789,738 | B2 | | 7/2014 | Knodel et al. | |
| 8,801,732 | B2 | | 8/2014 | Harris et al. | |
| 8,910,847 | B2 | | 12/2014 | Nalagatla et al. | |
| 9,016,541 | B2 | | 4/2015 | Viola et al. | |
| 9,186,142 | B2 | | 11/2015 | Fanelli et al. | |
| 9,192,387 | B1 | | 11/2015 | Holsten et al. | |
| 9,265,500 | B2 | | 2/2016 | Sorrentino et al. | |
| 9,402,628 | B2 | | 8/2016 | Beardsley | |
| 9,517,065 | B2 | | 12/2016 | Simms et al. | |
| 9,622,746 | B2 | | 4/2017 | Simms et al. | |
| 9,713,469 | B2 | | 7/2017 | Leimbach et al. | |
| 9,717,497 | B2 | | 8/2017 | Zerkle et al. | |
| 9,782,171 | B2 | | 10/2017 | Viola | |
| 9,795,379 | B2 | | 10/2017 | Leimbach et al. | |
| 9,808,248 | B2 | | 11/2017 | Hoffman | |
| 9,848,874 | B2 | | 12/2017 | Kostrzewski | |
| 9,907,552 | B2 | | 3/2018 | Measamer et al. | |
| 9,936,949 | B2 | | 4/2018 | Measamer et al. | |
| 10,092,292 | B2 | | 10/2018 | Boudreaux et al. | |
| 10,166,026 | B2 | | 1/2019 | Shelton, IV et al. | |
| 10,265,073 | B2 | * | 4/2019 | Scheib | A61B 17/068 |
| 10,285,705 | B2 | | 5/2019 | Shelton, IV et al. | |
| 10,327,764 | B2 | | 6/2019 | Harris et al. | |
| 10,463,368 | B2 | * | 11/2019 | Kostrzewski | A61B 17/0644 |
| 10,639,040 | B2 | | 5/2020 | Penna et al. | |
| 10,709,452 | B2 | | 7/2020 | DiNardo et al. | |
| 10,898,187 | B2 | | 1/2021 | Deck et al. | |
| 10,925,607 | B2 | | 2/2021 | Penna et al. | |
| 11,033,266 | B2 | | 6/2021 | Jones et al. | |
| 11,045,193 | B2 | | 6/2021 | Schings et al. | |
| 11,241,232 | B2 | | 2/2022 | Guerrera | |
| 11,284,890 | B2 | | 3/2022 | Nalagatla et al. | |
| 11,432,815 | B2 | | 9/2022 | Courtwright et al. | |
| 11,666,339 | B2 | | 6/2023 | Bruce et al. | |
| 11,911,039 | B2 | | 2/2024 | Boudreaux et al. | |
| 12,004,744 | B2 | | 6/2024 | Schings et al. | |
| 2002/0185517 | A1 | | 12/2002 | Vresh et al. | |
| 2003/0078603 | A1 | | 4/2003 | Schaller et al. | |
| 2004/0073237 | A1 | | 4/2004 | Leinsing | |
| 2006/0291981 | A1 | | 12/2006 | Viola et al. | |
| 2008/0082126 | A1 | | 4/2008 | Murray et al. | |
| 2008/0210738 | A1 | | 9/2008 | Shelton, IV et al. | |
| 2010/0191262 | A1 | | 7/2010 | Harris et al. | |
| 2011/0011916 | A1 | | 1/2011 | Levine | |
| 2012/0080339 | A1 | | 4/2012 | Shelton, IV et al. | |
| 2012/0080498 | A1 | | 4/2012 | Shelton, IV et al. | |
| 2012/0083836 | A1 | | 4/2012 | Shelton, IV et al. | |
| 2012/0241505 | A1 | | 9/2012 | Alexander, III et al. | |
| 2013/0172929 | A1 | | 7/2013 | Hess et al. | |
| 2014/0027493 | A1 | | 1/2014 | Jankowski | |
| 2014/0081176 | A1 | * | 3/2014 | Hassan | A61B 90/06 600/593 |
| 2014/0158747 | A1 | | 6/2014 | Measamer et al. | |
| 2014/0239037 | A1 | * | 8/2014 | Boudreaux | A61B 17/07207 227/175.1 |
| 2014/0263570 | A1 | * | 9/2014 | Hopkins | A61B 17/07207 227/176.1 |
| 2015/0083772 | A1 | | 3/2015 | Miller et al. | |
| 2015/0097019 | A1 | * | 4/2015 | Kostrzewski | A61B 17/07207 227/178.1 |
| 2015/0297236 | A1 | * | 10/2015 | Harris | A61B 17/068 227/176.1 |
| 2016/0270783 | A1 | * | 9/2016 | Yigit | A61B 17/072 |
| 2016/0278768 | A1 | | 9/2016 | Johnson et al. | |
| 2017/0119388 | A1 | | 5/2017 | Kostrzewski | |
| 2017/0119397 | A1 | | 5/2017 | Harris et al. | |
| 2017/0281187 | A1 | | 10/2017 | Shelton, IV et al. | |
| 2018/0132849 | A1 | | 5/2018 | Miller et al. | |
| 2018/0168599 | A1 | * | 6/2018 | Bakos | A61B 17/07207 |
| 2018/0168637 | A1 | | 6/2018 | Harris et al. | |
| 2018/0206844 | A1 | * | 7/2018 | Harris | A61B 17/07292 |
| 2018/0235613 | A1 | | 8/2018 | Shelton, IV et al. | |
| 2018/0235635 | A1 | | 8/2018 | Rekstad et al. | |
| 2018/0242974 | A1 | | 8/2018 | Guerrera et al. | |
| 2018/0325508 | A1 | | 11/2018 | Aronhalt et al. | |
| 2019/0000481 | A1 | | 1/2019 | Harris et al. | |
| 2019/0008518 | A1 | * | 1/2019 | Sgroi, Jr. | A61B 17/0643 |
| 2019/0328390 | A1 | | 10/2019 | Harris et al. | |
| 2020/0038017 | A1 | | 2/2020 | Hess et al. | |
| 2020/0046353 | A1 | | 2/2020 | Deck et al. | |
| 2020/0046355 | A1 | * | 2/2020 | Harris | A61B 17/105 |
| 2020/0054338 | A1 | * | 2/2020 | Shen | A61B 17/1155 |
| 2020/0054339 | A1 | | 2/2020 | Scirica et al. | |
| 2020/0205835 | A1 | | 7/2020 | Nalagatla et al. | |
| 2020/0229814 | A1 | | 7/2020 | Amariglio et al. | |
| 2020/0246001 | A1 | * | 8/2020 | Ming | A61B 17/00234 |
| 2020/0281595 | A1 | | 9/2020 | Wise et al. | |
| 2020/0337698 | A1 | | 10/2020 | Simms | |
| 2021/0038223 | A1 | | 2/2021 | Schings et al. | |
| 2021/0128150 | A1 | | 5/2021 | Hopkins et al. | |
| 2021/0307749 | A1 | * | 10/2021 | Shelton, IV | A61B 17/0644 |
| 2023/0045940 | A1 | | 2/2023 | Shelton, IV et al. | |
| 2023/0047471 | A1 | | 2/2023 | Jones et al. | |
| 2023/0049352 | A1 | | 2/2023 | Shelton, IV et al. | |
| 2023/0051305 | A1 | * | 2/2023 | Jones | A61B 17/0644 |
| 2023/0053080 | A1 | | 2/2023 | Jones et al. | |
| 2023/0107231 | A1 | | 4/2023 | Schings et al. | |

FOREIGN PATENT DOCUMENTS

| | | | |
|---|---|---|---|
| EP | 1875870 | A1 | 1/2008 |
| EP | 2157918 | A1 | 3/2010 |
| EP | 2540231 | A2 | 1/2013 |
| EP | 2649949 | A1 | 10/2013 |
| EP | 3000407 | A2 | 3/2016 |

(56) References Cited

FOREIGN PATENT DOCUMENTS

| | | | |
|---|---|---|---|
| EP | 3225176 | A1 | 10/2017 |
| EP | 3225179 | A1 | 10/2017 |
| EP | 3245958 | A1 | 11/2017 |
| EP | 3130292 | B1 | 8/2018 |
| EP | 3173030 | B1 | 10/2019 |
| EP | 3643252 | A1 | 4/2020 |
| RU | 2066128 | C1 | 9/1996 |
| WO | 1996/022055 | A1 | 7/1996 |
| WO | 2001/054594 | A1 | 8/2001 |
| WO | 2002/009595 | A1 | 2/2002 |
| WO | 2005/115254 | A2 | 12/2005 |
| WO | 2008/141288 | A1 | 11/2008 |
| WO | 2020/249487 | A1 | 12/2020 |
| WO | 2022/238841 | A2 | 11/2022 |

OTHER PUBLICATIONS

International Search Report and Written Opinion dated Nov. 14, 2022, for International Application No. PCT/IB2022/057444, 12 pages.

International Search Report and Written Opinion dated Jan. 27, 2023, for International Application No. PCT/IB2022/057446, 19 pages.

International Search Report and Written Opinion dated Nov. 23, 2022, for International Application No. PCT/IB2022/057449, 15 pages.

International Search Report and Written Opinion dated Jan. 25, 2023, for International Application No. PCT/IB2022/057442, 20 pages.

International Search Report and Written Opinion dated Nov. 14, 2022, for International Application No. PCT/IB2022/057443, 12 pages.

International Search Report and Written Opinion dated Nov. 24, 2022, for International Application No. PCT/IB2022/057451, 13 pages.

International Search Report and Written Opinion dated Dec. 14, 2022, for International Application No. PCT/IB2022/059023, 15 pages.

International Search Report and Written Opinion dated Dec. 19, 2022, for International Application No. PCT/IB2022/059020, 18 pages.

* cited by examiner

STAPLE AND STAPLE-FORMING POCKET ARRANGEMENTS FOR SURGICAL STAPLERS

PRIORITY

This application is a continuation of U.S. patent application Ser. No. 17/485,586, entitled "Staple and Staple-Forming Pocket Arrangements For Surgical Staplers," filed Sep. 27, 2021, issued as U.S. Pat. No. 12,004,744 on Jun. 11, 2024, the disclosure of which is incorporated by reference herein in its entirety.

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
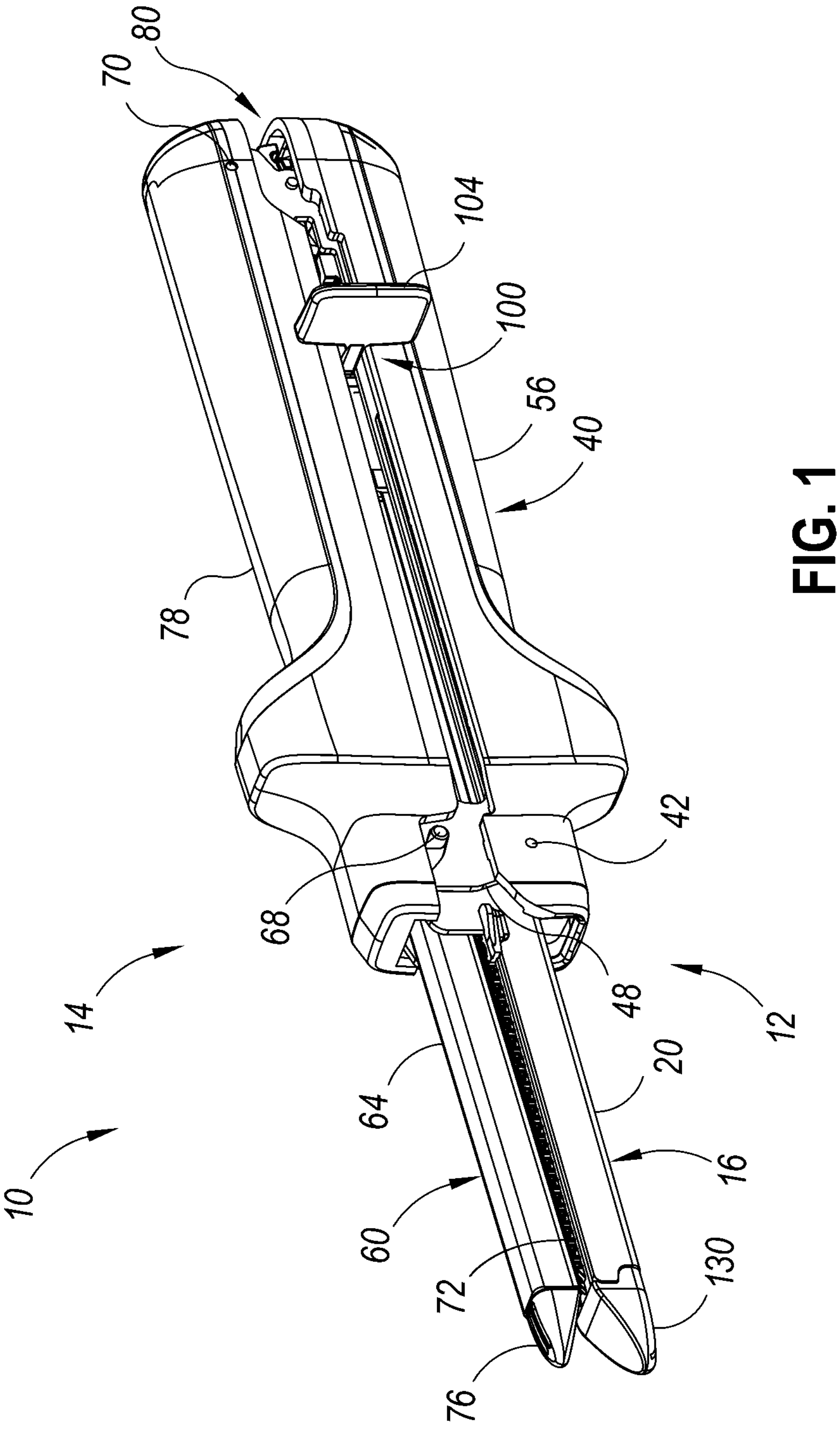
FIG. 1 depicts a perspective view of an exemplary linear surgical stapler, showing a cartridge half and an anvil half of the stapler coupled together with a clamp lever of the cartridge half in a fully closed position, where the anvil half includes an anvil and the cartridge half includes a staple cartridge.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
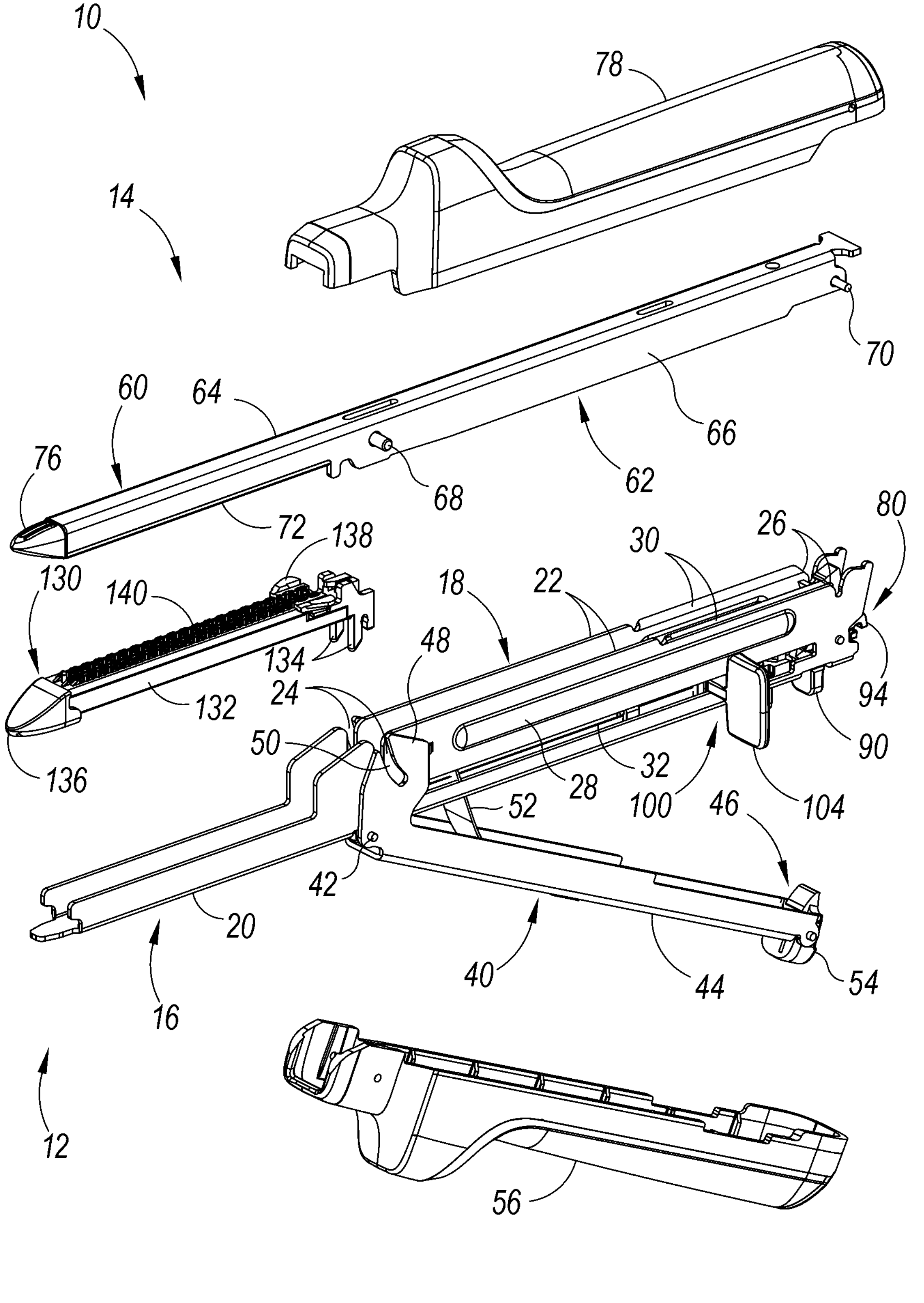
FIG. 2 depicts an exploded perspective view of the linear surgical stapler of FIG. 1.

FIGS. 1-2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) includes an elongate cartridge channel (16) having a proximal frame portion (18) and a distal jaw portion (20). Proximal frame portion (18) slidably retains a firing assembly (100) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (100) between proximal and distal positions. Firing assembly (100) is described in greater detail below in connection with FIG. 2. Distal jaw portion (20) of cartridge channel (16) is configured to receive a staple cartridge (130) (or "reload"), which may be configured in accordance with the teachings of U.S. Pat. App. No. 16/537,005, entitled "Linear Surgical Stapler," issued as U.S. Pat. No. 11,229,433 on Jan. 25, 2022, the disclosure of which is incorporated by reference herein.

Cartridge half (12) further includes a clamp lever (40) (also referred to as a "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Clamp lever (40) is operable to pivot relative to cartridge channel (16) between an open position in which proximal end (46) of lever arm (44) is spaced from cartridge channel frame portion (18), and a closed position in which proximal end (46) confronts cartridge channel frame portion (18). Actuation of clamp lever (40) from the open position to the closed position operates to capture the opposed lateral ends of latch pin (68) within clamp lever jaw slots (50), and thereby clamp anvil half (14) against cartridge half (12). In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a flat spring (52) biases lever arm (44) toward the open position. Accordingly, flat spring (52) promotes disengagement of clamp lever jaws (48) from anvil half latch pin (68) upon initial advancement of clamp lever (40) from the closed position toward the open position. As shown in FIG. 2, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired.

Anvil half (14) of linear surgical stapler (10) includes an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil pins (68, 70) are configured to facilitate coupling of anvil half (14) with cartridge half (12), as described below. Distal jaw portion (64) of anvil half (14) supports an anvil (72), shown as an anvil plate that defines an anvil surface having a plurality of staple forming pockets (184*a-b*)) (see FIG. 5) configured to deform legs of staples ejected by staple cartridge (130) when stapler (10) is fired, for example as described in greater detail in U.S. Pat. No. 11,229,433 issued on Jan. 25, 2022, incorporated by reference above. An elongate knife slot (186) extends longitudinally along anvil (72). In some versions, the anvil surface may be formed integrally with distal jaw portion (64). Distal jaw portion (64) of anvil half (14) additionally supports a tapered distal tip member (76). In some versions, distal tip member (76) may be selectively extendable relative to distal jaw portion (64) in accordance with the teachings of U.S. Pat. No. 11,033,266, entitled "Decoupling Mechanism for Linear Surgical Stapler," issued on Jun. 15, 2021, the disclosure of which is incorporated by reference herein.

As shown in FIG. 2, linear surgical stapler (10) further includes a plurality of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) in accordance with the teachings of U.S. Pat. No. 11,278,285, entitled "Clamping Assembly for Linear Surgical Stapler," issued on Mar. 22, 2022, the disclosure of which is incorporated by reference herein. It will be appreciated that in other versions, shrouds (56, 78) may be coupled with clamp lever (40) and anvil channel (60) in a variety of other suitable manners readily apparent to those of ordinary skill in the art.

As shown in FIG. 2, a proximal end of cartridge half (12) includes a retaining assembly (80) configured to releasably retain portions of anvil half (14) and firing assembly (100). Retaining assembly (80) of the present example includes an anvil latch member (82) and a detent member (84), both of which are rotatably coupled with a proximal end of cartridge channel (16) via a laterally extending pin (86) arranged proximally of firing slots (32). A torsion spring (not shown) is configured to resiliently bias anvil latch member (82) and detent member in opposite rotational directions about the lateral axis defined by pin (86). An anvil latch member releasably captures proximal anvil pin (70) when pin (70) is directed into proximal tapered notches (26) of cartridge channel (16), thereby coupling the proximal ends of stapler halves (12, 14). A lower end of the anvil latch member defines a release button (90) configured to be depressed by the operator when clamp lever (40) is in the open position to release proximal pin (70) and thereby permit separation of the proximal ends of stapler halves (12, 14). A proximal hook (94) is configured to releasably capture an upper tip of clamp lever latch member (54), thereby preventing actuation of clamp lever latch member (54) and opening of clamp lever (40) during firing of stapler (10). When firing assembly (100) is in its proximal home position (i.e., before or after firing of stapler (10)), proximal hook (94) permits clamp lever latch member (54) to rotatably disengage proximal frame portion (18) of cartridge channel (16) in response to actuation by the operator. As a result, clamp lever (40) may then be opened. Retaining assembly (80) and related components of cartridge half (12) may be further configured and operable in accordance with at least some of the teachings of U.S. Pat. No. 10,898,187, entitled "Firing System for Linear Surgical Stapler," issued on Jan. 26, 2021, the disclosure of which is incorporated by reference herein.

With continued reference to FIG. 2, firing assembly (100) of cartridge half (12) includes slide block (not shown), at least one actuator (104) (or "firing knob") pivotably coupled to slide block, and a plurality of elongate beams (not shown). Each actuator (104) of firing assembly (100) is configured and rotatable relative to the slide block between a deployed position and a retracted position such that only one actuator (104) may be deployed at a time, for example as described in greater detail in U.S. Pat. No. 10,898,187, incorporated by reference above. In the deployed position, an actuator (104) may be driven distally by an operator to actuate firing assembly (100) distally through stapler (10) and thereby simultaneously cut and staple tissue clamped between stapler halves (12, 14). Staple cartridge (130) and anvil (72) are shown and described in U.S. Pat. No. 11,045,193, entitled "Anvil Assembly for Linear Surgical Stapler," issued Jun. 29, 2021, the disclosure of which is incorporated by reference herein.

B. Overview of Exemplary Staple Cartridge

Figure 3:
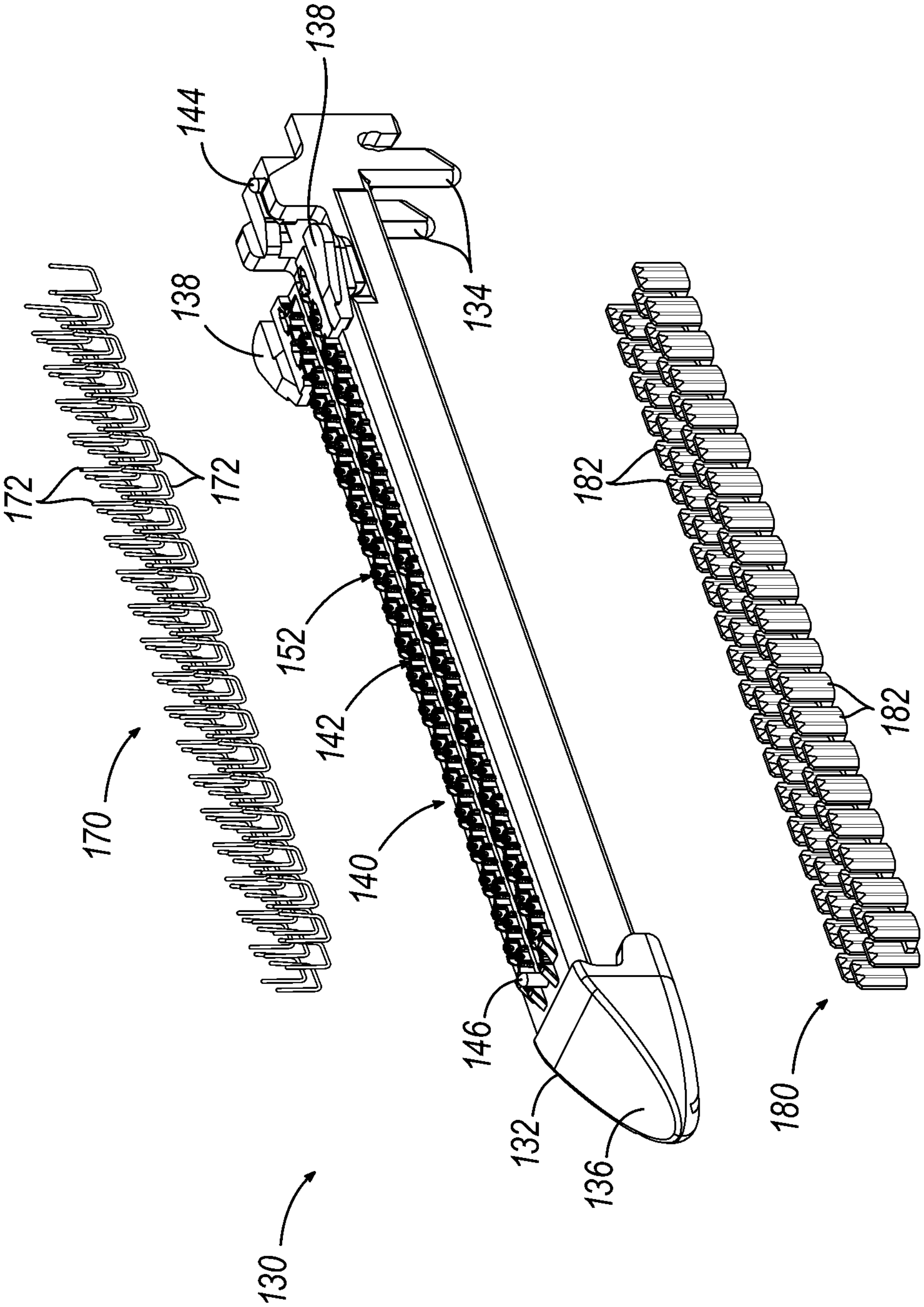
FIG. 3 depicts an exploded perspective view of the staple cartridge of FIG. 1.
Figure 4:
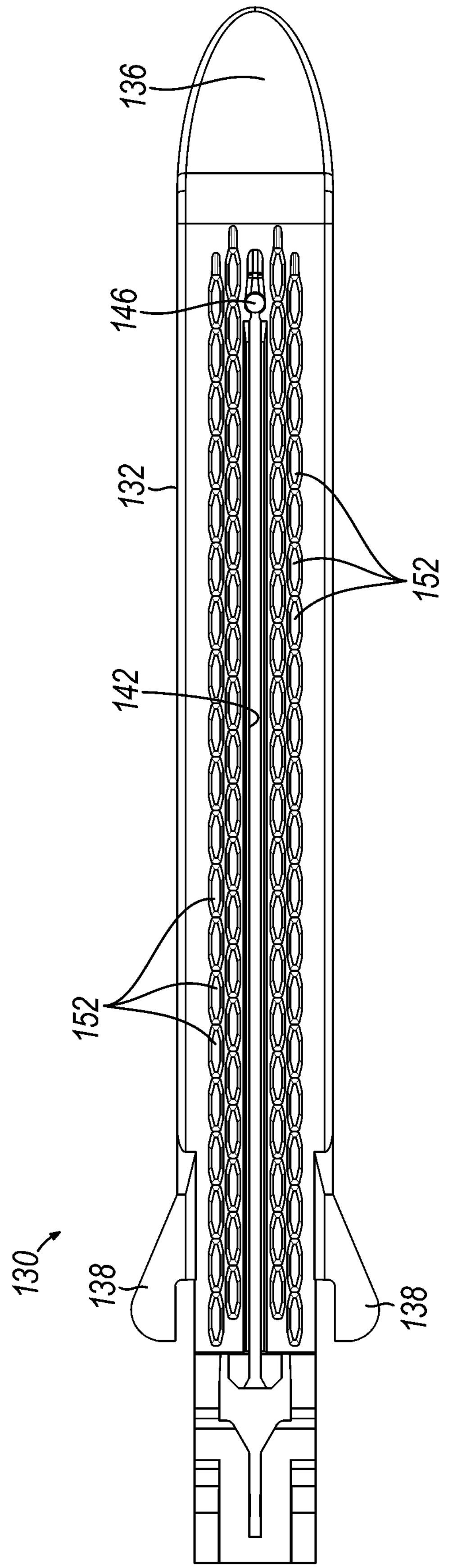
FIG. 4 depicts a top plan view of the staple cartridge of FIG. 1.

As shown in FIGS. 3 and 4, staple cartridge (130) includes an elongate cartridge body (132) extending linearly along a longitudinal axis between a proximal end having a pair of hooks (134) and a distal end having a tapered nose (136). Proximal hooks (134) are configured to releasably capture clamp lever pivot pin (42) and extend downwardly through corresponding openings formed in a floor of cartridge channel (16) when staple cartridge (130) is seated within distal jaw portion (20) of cartridge channel (16). A pair of wing tabs (138) disposed on the lateral sides of cartridge body (132) near the proximal end are configured to facilitate insertion and removal of staple cartridge (130) relative to distal jaw portion (20). An upper side of cartridge body (132) defines a deck (140). An elongate knife slot (142) extends longitudinally through cartridge deck (140) along the longitudinal axis of staple cartridge (130) and is configured to slidably receive knife member (116) of firing assembly (100) therethrough in response to distal actuation thereof, described above. A rigid tissue gap post (146) is secured at a distal end of the knife slot and protrudes upwardly away from cartridge deck (140). A rounded upper end of tissue gap post (146) is configured to contact a distal end of anvil (72) and thereby define a tissue gap between cartridge deck (140) and anvil (72) when stapler halves (12, 14) are clamped together in the manner described below. FIG. 4 shows a top plan view of staple cartridge (130) of FIG. 1. Cartridge deck (140) defines a plurality of staple cavities (152), which are shown as protruding from cartridge deck (140). Each staple cavity (152) houses an arrangement (170) of staples (172) and a respective arrangement (180) of staple drivers (182). Staple cartridge (130) may be configured in accordance with the teachings of U.S. Pat. No. 11,229,433, incorporated by reference above.

II. Exemplary Staple Cartridges and Exemplary Anvils

It may be desirable to modify staple cartridge (130) and/or anvil (72) described above to increase staple density while minimizing misalignments between unformed staples (172) and staple forming pockets (184*a-b*). As used herein, staple density is intended to refer to the number of staples per unit area of the staple cartridge. Higher staple density may provide increased seal strength against luminal leakage through the formed staple pattern and/or provide increased mechanical securing of the stapled tissue. It is also beneficial to reduce time and associated costs of manufacturing, inspecting, and qualifying anvil (72) for use with stapler (10) of FIG. 1. It may also be desirable to reduce the dimensions of anvil (72) while still providing adequate stapling functionality so that stapler (10) may more easily access the desired anatomy of the patient.

It is envisioned that any of exemplary staples (230*a-b*, 330, 430*a-b*, 510, 828*a-b*, 844*a-b*, 910, 1010) may be used with any exemplary staple cartridge (210, 310) and any exemplary anvil (212, 412, 612, 712, 810). Staples (230*a-b*, 330, 430*a-b*, 510, 910, 1010) may be incorporated into a stapling assembly (e.g., staple cartridges (210, 310)), which may include features similar to staple cartridge (130) shown and described above with reference to FIGS. 1-4. Anvils (212, 412, 612, 712, 810) may require reduced time and associated costs of manufacturing, inspecting, and qualifying of anvils (212, 412, 612, 712, 810) using exemplary staple forming pockets (246, 248, 446, 448, 449, 451, 646, 648, 746, 748, 749, 751, 816, 818, 820, 822). As described below, staple forming pockets (246, 248, 446, 448, 449, 451, 646, 648, 746, 748, 749, 751, 816, 818, 820, 822) extend continuously to deform at least a portion of multiple staples (230*a-b*, 330, 430*a-b*, 510, 828*a-b*, 844*a-b*, 910, 1010).

While the above examples are provided in the context of a linear surgical stapler, it should be understood that the following teachings may be readily applied to any other suitable kinds of staplers, including but not limited to endocutters, linear surgical staplers, circular surgical staplers, right angle surgical staplers, and curved surgical staplers, for example. For example, the teachings of this application may be combined with various exemplary endocutters, such that those shown and described in U.S. Pat. No. 9,517,065, entitled "Integrated Tissue Positioning and Jaw Alignment Features for Surgical Stapler," issued Dec. 13, 2016; U.S. Pat. No. 9,808,248, entitled "Installation Features for Surgical Instrument End Effector Cartridge," issued Nov. 7, 2017; and/or U.S. Pat. No. 10,092,292, entitled "Staple Forming Features for Surgical Stapling Instrument," issued Oct. 9, 2018, the disclosure of each which is incorporated by reference herein. The teachings of this application may be combined with various exemplary linear surgical staplers, such that those shown and described in U.S. Pat. No. 11,045,193, entitled "Anvil Assembly for Linear Surgical Stapler," issued Jun. 29, 2021, the disclosure of which is incorporated by reference herein. The teachings of this application may be combined with various exemplary circular surgical staplers, such that those shown and described in U.S. Pat. No. 10,709,452, entitled "Methods and Systems for Performing Circular Stapling," issued Jul. 14, 2020; U.S. Pub. No. 2018/0132849, entitled "Staple Forming Pocket Configurations for Circular Surgical Stapler Anvil," published May 17, 2018, now abandoned; U.S. Pat. No. 11,406,379, entitled "Surgical End Effectors with Staple Cartridges," issued on Aug. 9, 2022 and/or U.S. application Ser. No. 17/401,391, entitled "Methods of Forming an Anastomosis Between Organs with an Expandable Staple Pattern", filed Aug. 13, 2021, issued as U.S. Pat. No. 12,256,934 on Mar. 25, 2025, the disclosure of each of which is incorporated by reference herein. The teachings of this application may be combined with various exemplary right angle surgical staplers, such that those shown and described in U.S. Pat. No. 11,266,403, entitled "Tissue Cutting Washer for Right Angle Surgical Stapler," issued on Mar. 8, 2022, the disclosure of which is incorporated by reference herein. The teachings of this application may be combined with various exemplary curved surgical staplers, such that those shown and described in U.S. application Ser. No. 16/945,042, entitled "Features to Enhance Staple Height Consistency in Curved Surgical Stapler," filed Jul. 31, 2020, issued as U.S. Pat. No. 11,432,815 on Sep. 6, 2022, the disclosure of which is incorporated by reference herein.

Any one or more of the teachings, expressions, embodiments, examples, etc. described herein may be combined with any one or more of the teachings, expressions, embodiments, examples, etc. described in U.S. patent application Ser. No. 17/485,589, entitled "Overlapping Staple Pattern for Surgical Stapler," filed on Sep. 27, 2021, issued as U.S. Pat. No. 12,453,553 on Oct. 28, 2025, the disclosure of which is incorporated by reference herein.

Figure 6:
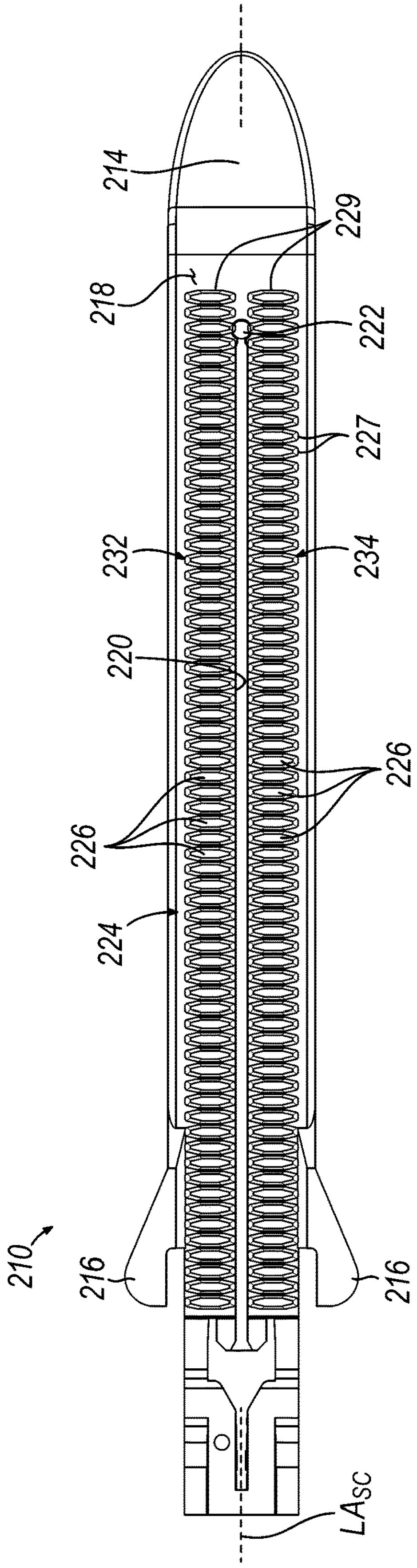
FIG. 6 depicts a top plan view of a first exemplary alternative staple cartridge, which may be incorporated into the stapler of FIG. 1.

A. First Exemplary Alternative Staple Cartridge with First Exemplary Alternative Staples and First Exemplary Alternative Anvil FIGS. 6-8B and 10 show a stapling assembly in the form a first exemplary alternative staple cartridge (210) and a first exemplary alternative anvil (212). Particularly, FIG. 6 shows a top plan view of staple cartridge (210), which may be incorporated into cartridge half (12) of stapler (10) of FIG. 1 in place of staple cartridge (130). Similar to staple cartridge (130), staple cartridge (210) includes a tapered nose (214), wing tabs (216), a cartridge deck (218), an elongate knife slot (220), a tissue gap post (222), an arrangement (224) of staple cavities (226), an arrangement (228) of first exemplary alternative staples (230*a-b*), an arrangement of staple drivers (not shown) but which may be similar to arrangement (180) of staple drivers (182), and a pair of proximal hooks (not shown). Unlike staple cartridge (130), arrangement (224) of staple cavities (226), arrangement (228) of staples (230*a-b*), and the arrangement of staple drivers (not shown) are positioned in an alternative manner to increase staple density as described below. Staple cartridge (210) extends along a longitudinal axis ($LA_{SC}$). Arrangement (224) of staple cavities (226) includes a first row (232) of staple cavities (226) and a second row (234) of staple cavities (226). Each staple cavity (226) has a long axis (227) and a short axis (229), where short axis (229) is perpendicular to long axis (227). As shown, short axis (229) extends longitudinally parallel to longitudinal axis ($LA_{SC}$), and the long axis (227) extends perpendicular to longitudinal axis ($LA_{SC}$). Staple cavities (226) may project out from cartridge deck (218) toward anvil (212).

Figure 7:
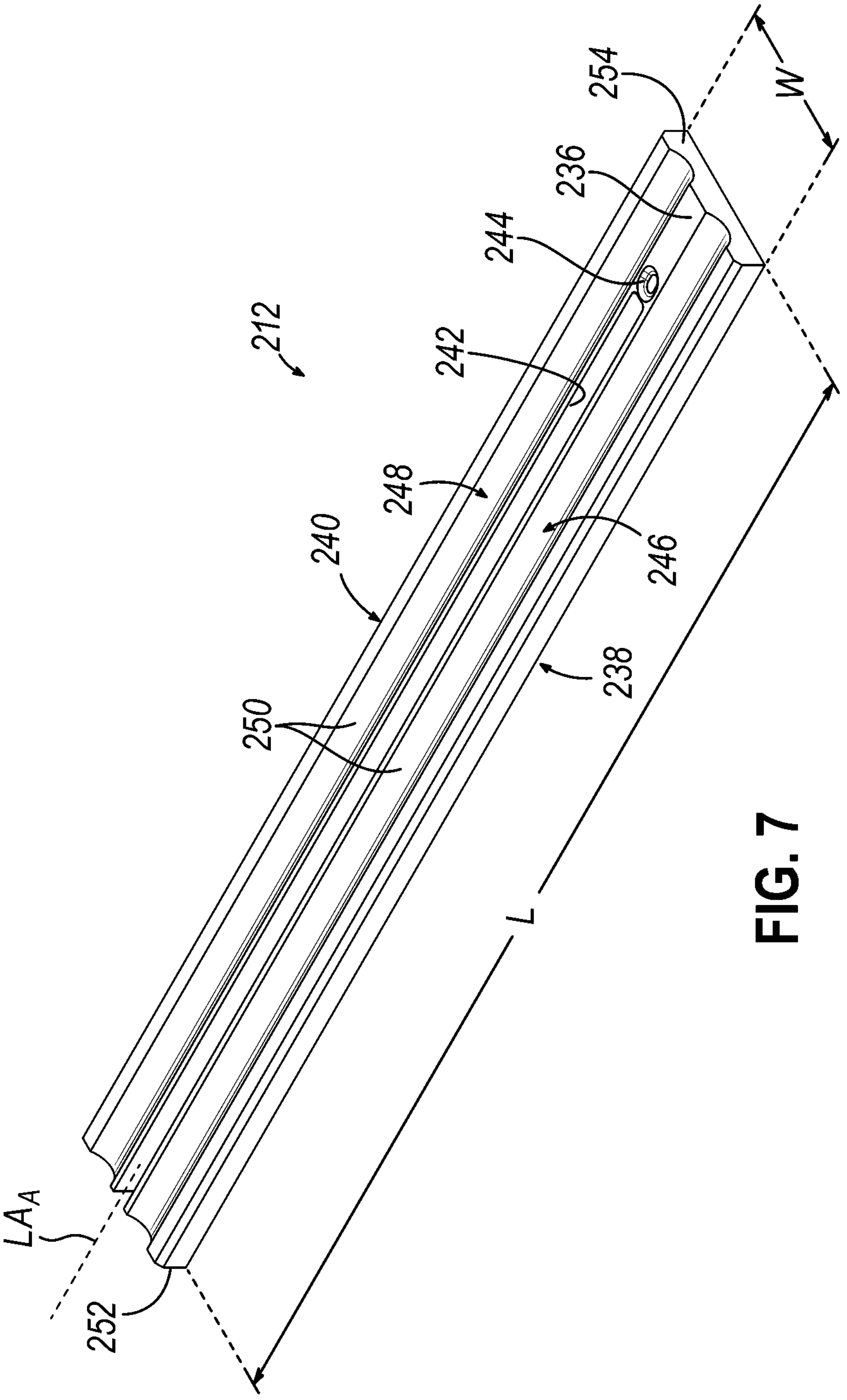
FIG. 7 depicts a perspective view of a first exemplary alternative anvil which may be incorporated into the stapler of FIG. 1.

FIG. 7 shows a perspective view of anvil (212) which may be incorporated into stapler (10) of FIG. 1 in place of anvil (72). Anvil (212) is shown in the form of an anvil plate which may be incorporated into anvil half (14). Anvil (212)

includes a distal connecting portion (236), a first lateral portion (238), and a second lateral portion (240). First and second lateral portions (238, 240) are separated by an elongate knife slot (242) that is configured to receive a knife member (184). Distal connecting portion (236) includes an aperture (244) configured to receive a pin to align anvil (212) with anvil half (14). Anvil (212) includes at least one staple forming pocket. As shown, anvil (212) includes first and second staple forming pockets (246, 248); however, additional staple forming pockets are also envisioned. First and second staple forming pockets (246, 248) extend continuously along a length (L) of anvil (212) from a proximal end (252) of anvil (212) to a distal end (254) of anvil (212). In other words, first and second staple forming pockets (246, 248) include a continuous elongate channel extending parallel to longitudinal axis ($LA_A$) of anvil (212) from proximal end (252) to distal end (254). First and second staple forming pockets (246, 248) extend parallel to one another and parallel to elongate knife slot (242). First and second staple forming pockets (246, 248) are shown as being generally semi-circular shape (250). Shapes of first and second staple forming pockets (246, 248) may vary. Anvil (212) is shown as being integrally formed together as a unitary piece.

Figure 8A:
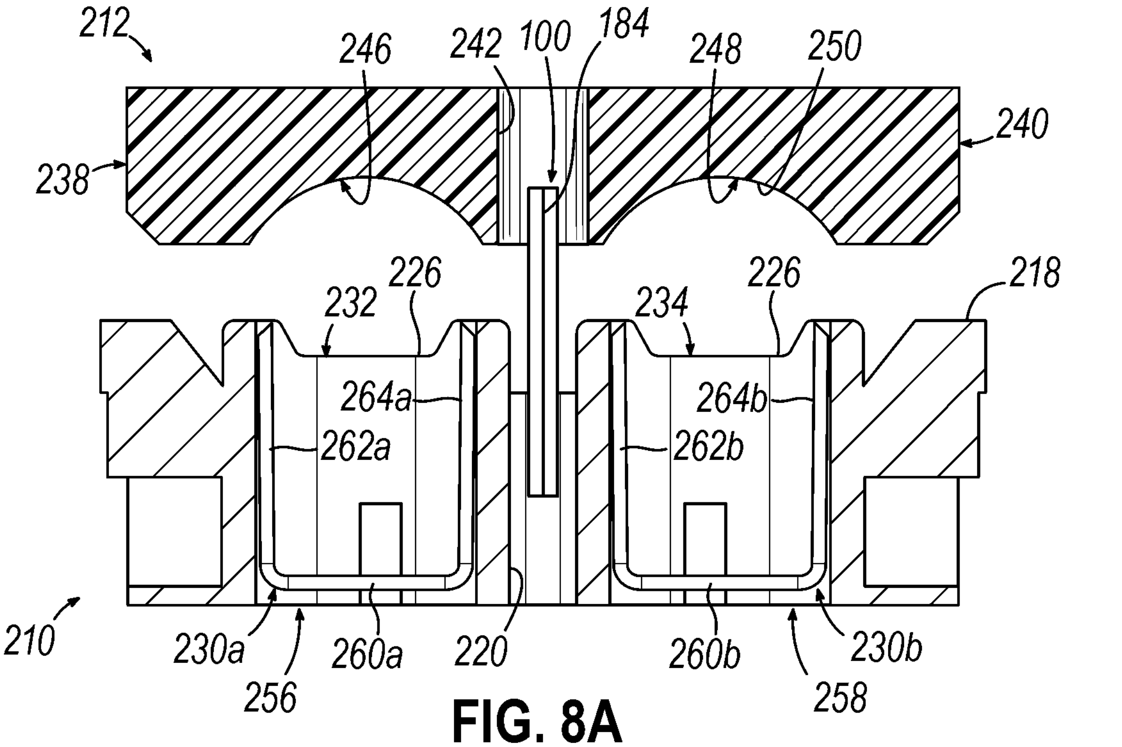
FIG. 8A depicts a schematic sectional view of first exemplary alternative staples disposed in the staple cartridge of FIG. 6 in a non-deformed state prior to contacting the anvil of FIG. 7.
Figure 8B:
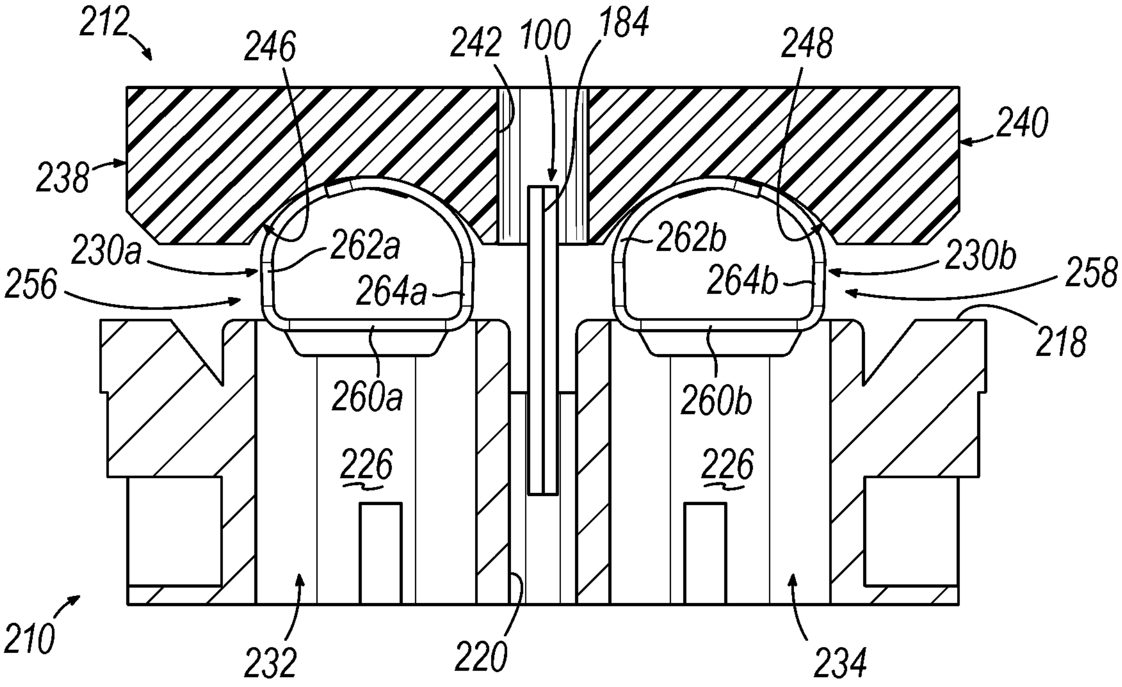
FIG. 8B depicts a schematic sectional view of the staples, the staple cartridge, and the anvil of FIG. 8A, but with the staples in a deformed state.

FIG. 8A shows a schematic view of staples (230*a*-*b*) disposed in staple cartridge (210) of FIG. 6 in a non-deformed state prior to contacting anvil (212) to deform staples (230*a*-*b*) to the deformed state shown in FIG. 8B. First staple forming pocket (246) is configured to align with first row (232) of staple cavities (226) and second staple forming pocket (248) is configured to align with second row (234) of staple cavities (226). Firing assembly (100) includes a knife member (184) (shown schematically in FIGS. 8A-8B) that is configured to traverse through elongate knife slots (220, 242) to sever tissue of a patient along a cut line (CL). Staples (230*a*) include crowns (260*a*) and first and second legs (262*a*, 264*a*). Similarly, staples (230*b*) include crowns (260*b*) and first and second legs (262*b*, 264*b*).

First staple forming pocket (246) of anvil (212) is configured to transition first and second legs (262*a*, 264*a*) of staples (230*a*) from first row (256) from the non-deformed state to the deformed state with the same firing stroke. As used herein, the same firing stroke is intended to include where staples are simultaneously deformed or sequentially deformed. For example, simultaneously deformed staples may be longitudinally adjacent one another (e.g., staples (230*a*-*b*) shown in FIGS. 8A-8B). For example, sequentially deformed staples may be disposed either proximal or distal to adjacent staples. Particularly, a first staple disposed proximal to a second staple may be deformed prior to second staple being deformed in the same firing stroke. Second staple forming pocket (248) of anvil (212) is configured to transition first and second legs (262*b*, 264*b*) of staples (230*b*) from second row (258) from the non-deformed state to the deformed state with the same firing stroke. In other words, the same first staple forming pocket (246) is configured to deform first and second legs (262*a*, 264*a*) of staples (230*a*) from first row (256), and the same second staple forming pocket (248) is configured to deform first and second legs (262*b*, 264*b*) of staples (230*b*) from second row (258). As a result, there is not a 1:1 correlation between staples (230*a*-*b*) and staple forming pockets (246, 248). Staples (230*a*-*b*) extend perpendicular to longitudinal axis ($LA_{SC}$) of staple cartridge (210). As shown, crowns (260*a*-*b*) of staples (230*a*-*b*) are oriented perpendicular to elongate knife slots (220, 242) traversed by knife member (184). Staples crowns (260*a*-*b*) of staples (230*a*-*b*) are pushed out of staple cavities (226) using staple drivers (not shown), but which may be similar to staple drivers (182) arranged to correspond to staple cavities (226).

Figure 5:
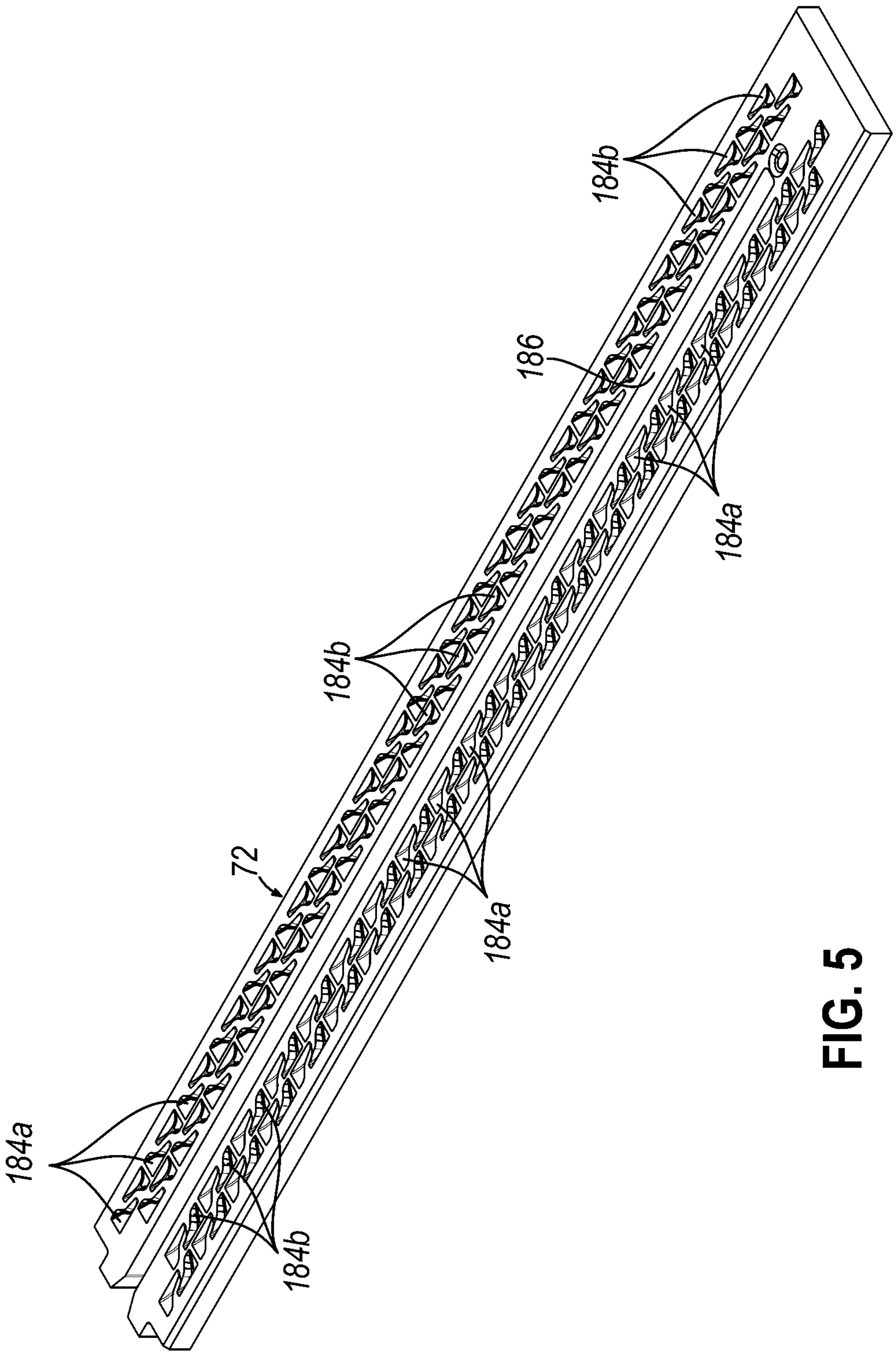
FIG. 5 depicts a perspective view of the anvil of FIG. 1.
Figure 9:
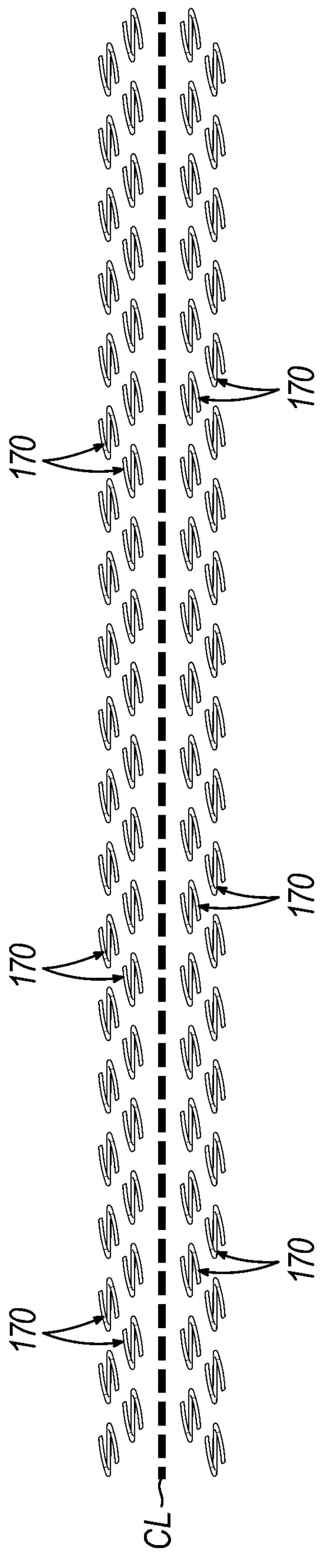
FIG. 9 depicts a top plan view of the arrangement of staples of FIG. 3 but in the deformed state using the anvil of FIG. 5.

FIG. 9 shows a top plan view of arrangement (170) of staples (172) of FIG. 3, but in the deformed state using anvil (72) of FIG. 5. As shown, staples (172) are oriented parallel with a cut line (CL) to provide hemostasis (i.e., prevent blood from passing through to cut line). This hemostasis is increased when two or more rows of staples (172) are staggered relative to each other as shown in FIG. 9. However, arrangement (170) of staples (172) of FIG. 9 oriented parallel with cut line (CL) does not maximize the number of staples (172) per inch along the length of cut line (CL). Increased staple density along the length of cut line (CL) may provide enhanced structural integrity of the staple line. A balance between hemostasis and perfusion may be desired. Allowing some perfusion reduces a potential risk of necrosis, as necrosis may result if blood flow to the tissue is completely cut off. However, it is desirable to have a degree of hemostasis so that tissue stops bleeding at cut line (CL). In other words, it may be desirable for cut tissue to receive blood, but not for the cut tissue to leak blood.

Figure 10:
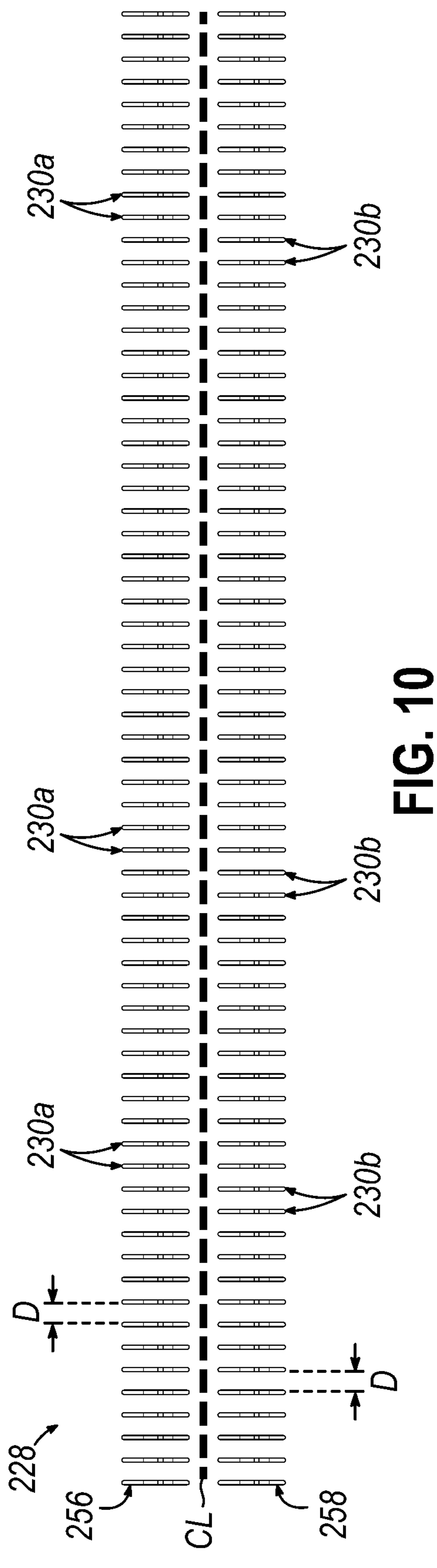
FIG. 10 depicts a top plan view of an arrangement of the staples of FIG. 8B.

First and second rows (256, 258) of staples (230*a*-*b*) are shown in FIG. 10. FIG. 10 shows a top plan view of arrangement (228) of staples (230) of FIG. 8B. It is desirable to increase staple density without increasing a width (W) of staple cartridge (210). As shown by comparing FIG. 9 with FIG. 10, staple cartridge (210) effectively provides six rows of staples within 4 rows of staple space. Particularly, FIG. 9 shows 80 staples, and FIG. 10 shows 132 staples (230*a*-*b*), which represents a 65% increase in staples without increasing the footprint occupied by staples (230*a*-*b*). While FIG. 10 shows a particular arrangement (228) of staples (230); other suitable arrangements of staples (230) are envisioned that may include more or fewer staples (230). Comparing staples (172) of FIG. 9 with staples (230*a*-*b*) of FIG. 10, distance (D) between longitudinally adjacent staples (230*a*-*b*) is reduced in FIG. 10. First and second rows (256, 258) of staples (230*a*-*b*) allow for a balance between hemostasis and perfusion.

Figure 11:
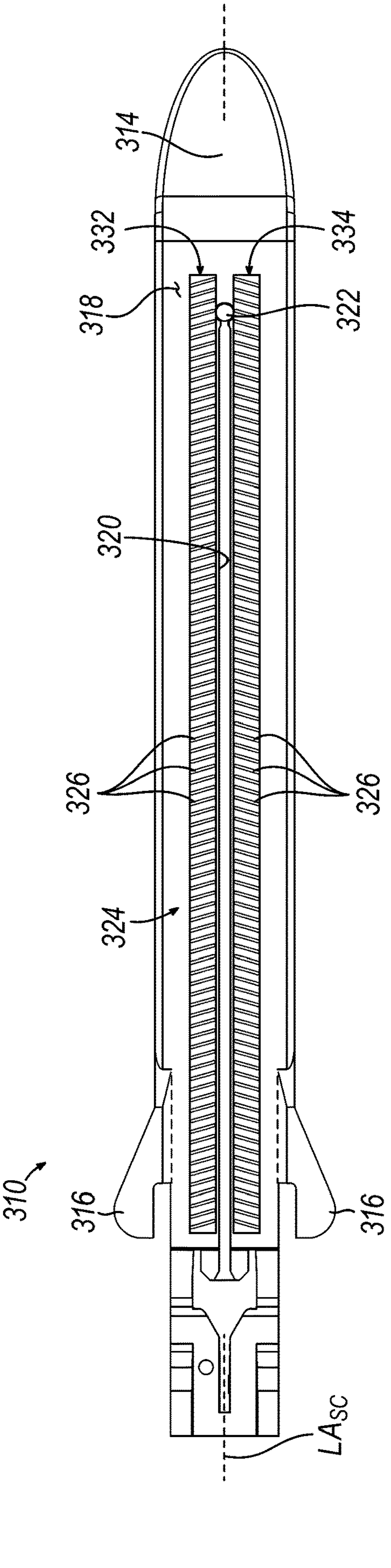
FIG. 11 depicts a top plan view of a second exemplary alternative staple cartridge, which may be incorporated into the stapler of FIG. 1.
Figure 13:
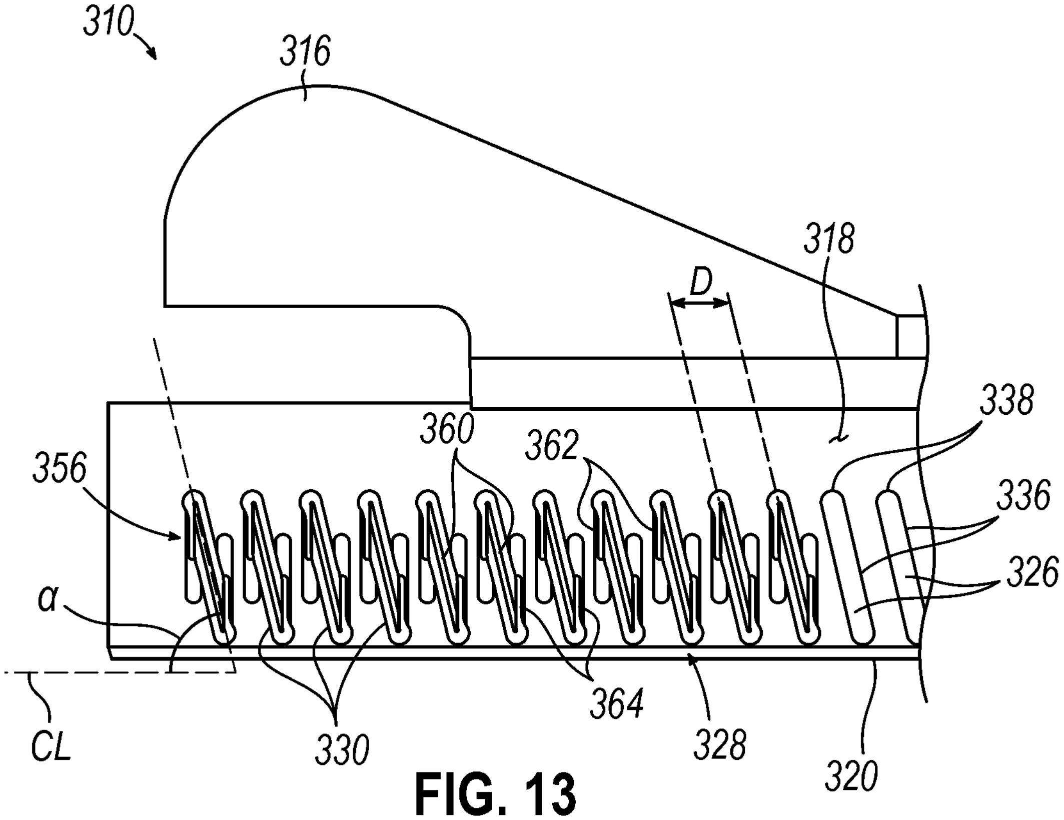
FIG. 13 depicts a partial top plan view of second exemplary alternative staples in the deformed state using the staple cartridge of FIG. 11 and the anvil of FIG. 7.

B. Second Exemplary Alternative Staple Cartridge and Second Exemplary Alternative Staple FIGS. 11 and 13 show a stapling assembly in the form a second exemplary alternative staple cartridge (310) that is configured for use with stapler (10), instead of staple cartridge (130). Staple cartridge (310) is shown and described in conjunction with anvil (212) instead of anvil (72); however, other suitable anvils are also envisioned. Similar to staple cartridge (130), staple cartridge (310) includes a tapered nose (314), wing tabs (316), a cartridge deck (318), an elongate knife slot (320), a tissue gap post (322), an arrangement (324) of staple cavities (326), an arrangement (328) of staples (330), an arrangement of staple drivers (not shown) but which may be similar to arrangement (180) of staple drivers (182), and a pair of proximal hooks (not shown).

Unlike staple cartridge (130) but similar to staple cartridge (210), arrangement (324) of staple cavities (326), arrangement (328) of staples (330), and an arrangement of staple drivers (not shown) are positioned in an alternative manner to increase staple density as described below. Staple cartridge (310) extends along a longitudinal axis ($LA_{SC}$). Arrangement (324) of staple cavities (326) includes a first row (332) of staple cavities (326) and a second row (334) of staple cavities (326). Unlike first and second rows (232, 234), staple cavities (226) are obliquely oriented relative to elongate knife slots (242, 320). Knife member (184) of firing assembly (100) is configured to traverse through elongate knife slots (242, 320) to sever tissue of a patient along a cut line (CL). Each staple cavity (326) has a long axis (336) and a short axis (338), where long and short axes (336, 338) extend at a non-zero angle (shown as angle (a)) relative to longitudinal axis ($LA_{SC}$). In some versions, staple cavities (326) may project out from cartridge deck (318) toward anvil (212).

Figure 12:
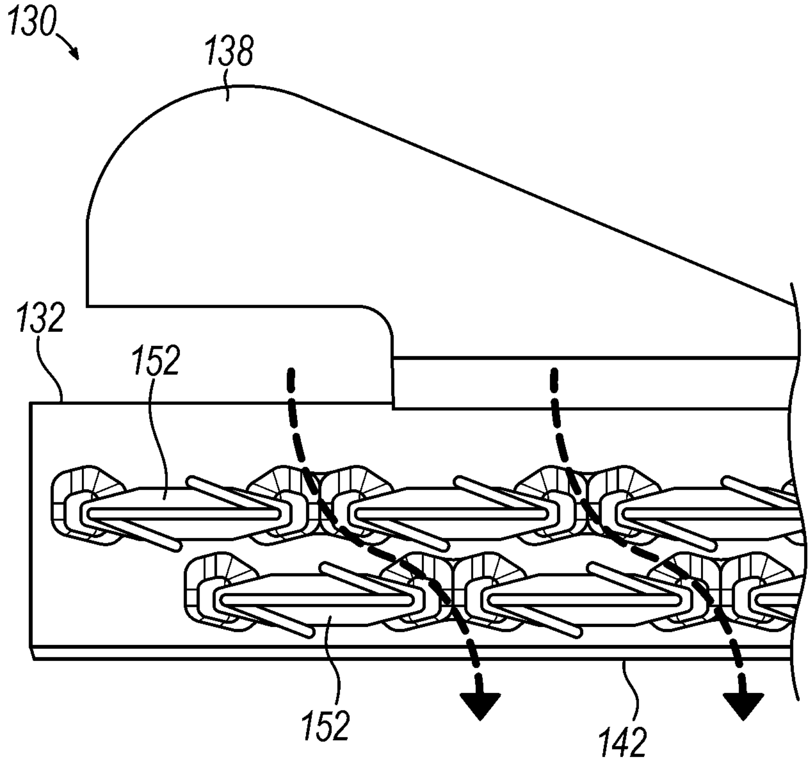
FIG. 12 depicts a partial top plan view of staples of FIG. 9 relative to staple cavities of the staple cartridge of FIG. 1.

FIGS. 12 and 13 show comparisons of portions of staple cartridges (130, 310) relative to staples (152, 330) for representative purposes. Particularly, FIG. 12 shows a partial top plan view of staples (172) of FIG. 9 in the deformed state relative to staple cavities (152) of staple cartridge (130) of FIG. 1. Arrows in FIG. 12 show potential fluid leak paths due to the spacing of staple cavities (152). FIG. 13 shows a partial top plan view of second exemplary alternative staples (330) relative to cartridge deck (318) of staple cartridge (310) of FIG. 11 in the deformed state. Staples (330) each include crown (360) and first and second legs (362, 364). Staple cavities (226) are obliquely oriented relative to elongate knife slots (242, 320) so as to angle first and second legs (362, 364) of staples (330) in a three-dimensional orientation in the deformed state. The oblique orientation of crowns (360) of staples (330) in cartridge deck (318) promote three-dimensional formation of staples (330). As a result, in the deformed state, first and second legs (362, 364) are not co-planar like arrangement (228) of staples (230) of FIG. 10.

First staple forming pocket (246) of anvil (212) is configured to transition first and second legs (362, 364) of staples (330) from first row (356) from the non-deformed state to the deformed state with the same firing stroke. Second staple forming pocket (348) of anvil (212) is configured to transition first and second legs (362, 364) of staples (330) from the second row (not shown) from the non-deformed state to the deformed state with the same firing stroke. Crowns (360) of staples (330) are oriented at a non-zero angle relative to elongate knife slots (242, 320) traversed by knife member (184). Increased staple density along the length of cut line (CL) may provide enhanced structural integrity of the staple line. Parallel-to-cut-line staples (FIGS. 9 and 12) may provide greater hemostasis, while perpendicular-to-cut-line staples (FIGS. 10 and 13) may provide greater perfusion. Comparing staples (172) of FIG. 12 with staples (330) of FIG. 13, distance (D) between adjacent staples (330) is reduced in FIG. 13.

Figure 14:
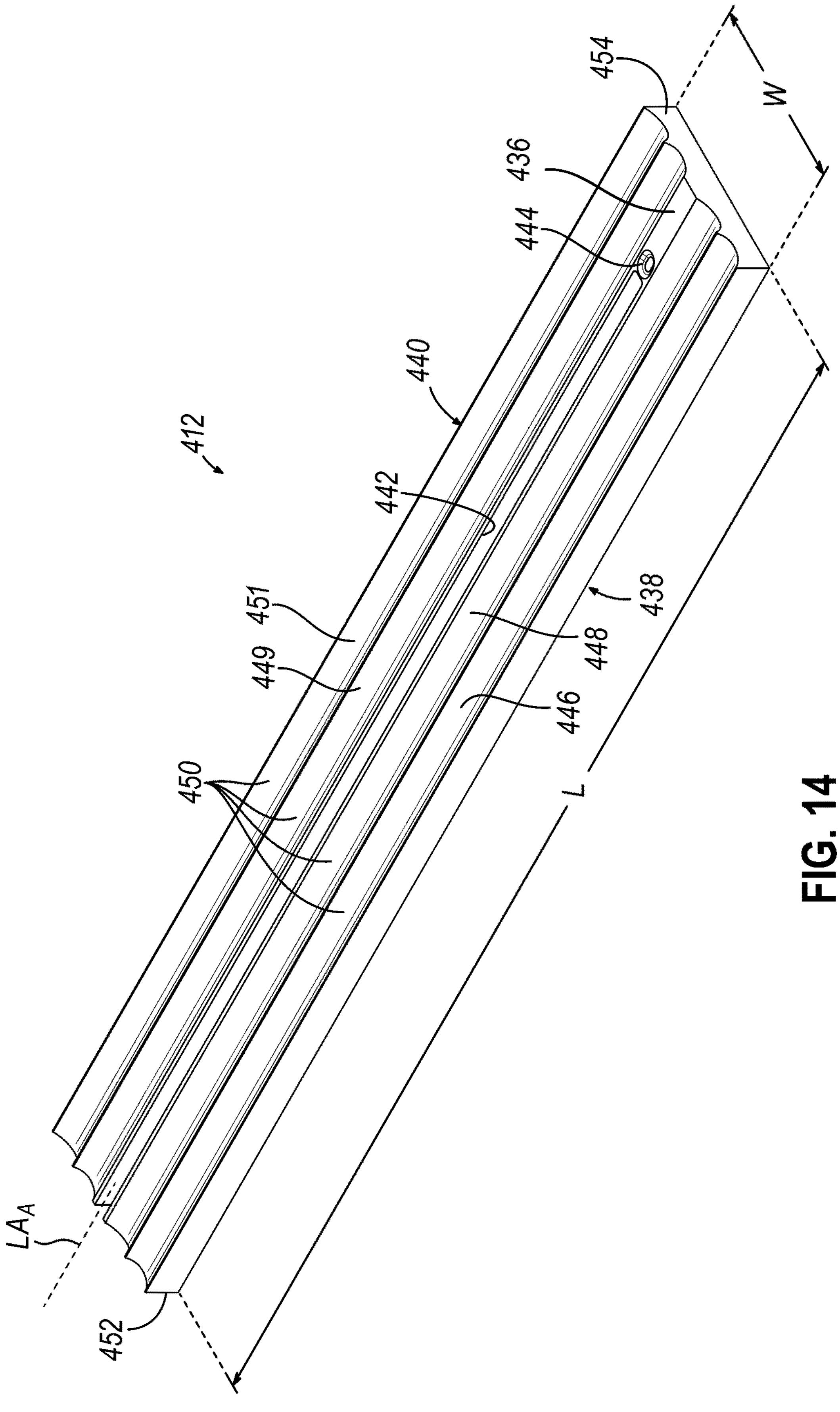
FIG. 14 depicts a perspective view of a second exemplary alternative anvil which may be incorporated into the stapler of FIG. 1.

C. Second Exemplary Alternative Anvil and Third Exemplary Alternative Staple FIGS. 14-15B show a second exemplary alternative anvil (412) which may be incorporated into stapler (10) shown and described above, along with staple cartridge (210) instead of staple cartridge (130). Anvil (412) is shown in the form of an anvil plate. Anvil (412) includes a distal connecting portion (436), a first lateral portion (438), and a second lateral portion (440). First and second lateral portions (438, 440) are separated by an elongate knife slot (442) that is configured to receive a knife member (184). Distal connecting portion (436) includes an aperture (444) configured to receive a pin to align anvil (412) with anvil half (14). Anvil (412) includes at least one staple forming pocket. Unlike anvil (212) which includes first and second staple forming pockets (246, 248), anvil (412) includes first, second, third, and fourth staple forming pockets (446, 448, 449, 451). First, second, third, and fourth staple forming pockets (446, 448, 449, 451) extend continuously along a length (L) of anvil (412) from a proximal end (452) of anvil (412) to a distal end (454) of anvil (412). In other words, first, second, third, and fourth staple forming pockets (446, 448, 449, 451) each include a continuous elongate channel extending parallel to longitudinal axis ($LA_A$) of anvil (412). First, second, third and fourth staple forming pockets (446, 448, 449, 451) extend parallel to one another and perpendicular to elongate knife slot (442). First and second staple forming pockets (446, 448) are shown on first lateral portion (438), and third and fourth staple forming pockets (449, 451) are shown on second lateral portion (440). Anvil (412) is shown as being integrally formed together as a unitary piece.

Figure 15A:
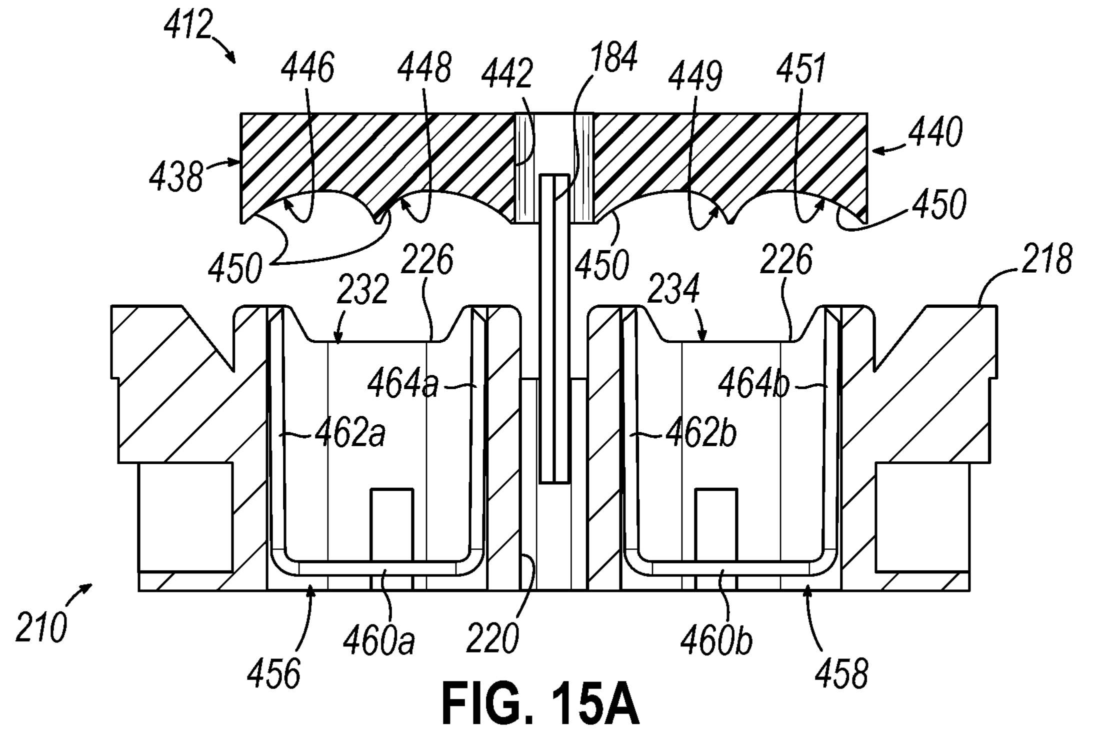
FIG. 15A depicts a schematic sectional view of third exemplary alternative staples disposed in the staple cartridge of FIG. 6 in a non-deformed state prior to contacting the anvil of FIG. 14.
Figure 15B:
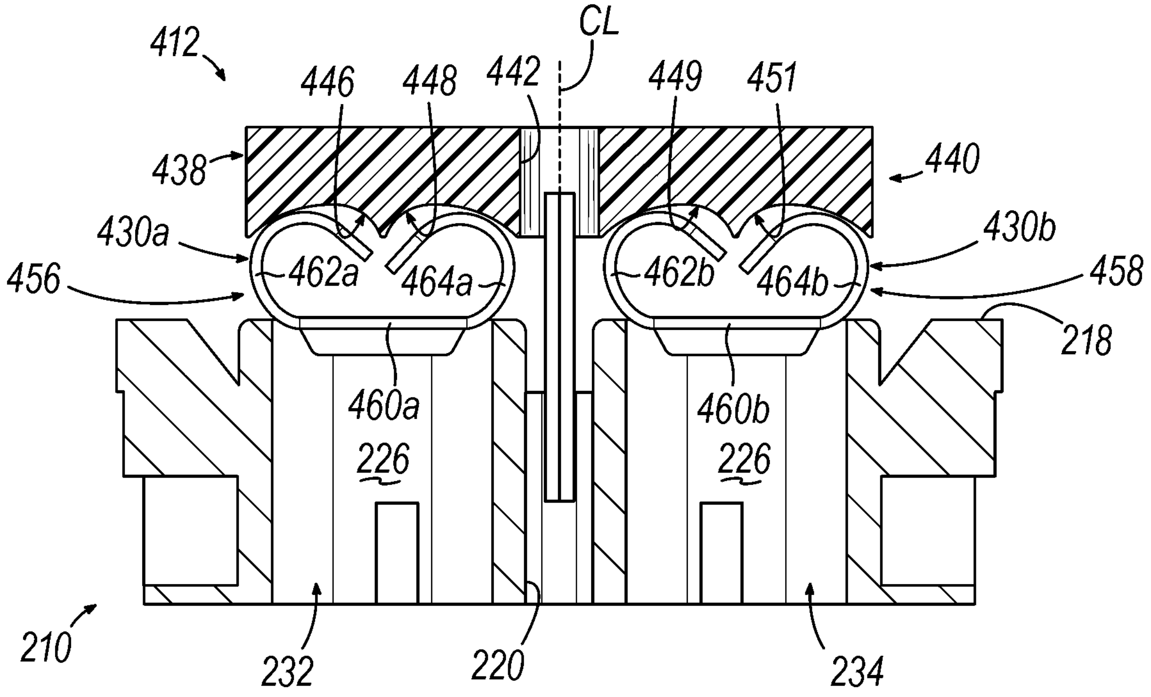
FIG. 15B depicts a schematic sectional view of the staples, the staple cartridge, and the anvil of FIG. 15A, but with the staples in a deformed state.

FIG. 15A shows a schematic sectional view of third exemplary alternative staples (430*a*-*b*) disposed in staple cartridge (210) of FIG. 6 in a non-deformed state prior to contacting anvil (412) in FIG. 15B to deform staples (430*a*-*b*) to a deformed state. Using first, second, third, and fourth staple forming pockets (446, 448, 449, 451) may deform staples (430*a*-*b*) differently than first and second staple forming pockets (246, 248). Firing assembly (100) includes a knife member (184) (shown schematically in FIGS. 15A-15B) that is configured to traverse through elongate knife slots (220, 442) to sever tissue of a patient along a cut line (CL). First and second rows (456, 458) of staples (430*a*-*b*) are shown in FIGS. 15A-15B. Staples (430*a*) include crowns (460*a*) and first and second legs (462*a*, 464*a*). Similarly, staples (430*b*) include crowns (460*b*) and first and second legs (462*b*, 464*b*). While not shown, staples crowns (460*a*-*b*) of staples (430*a*-*b*) are pushed out of staple cavities (226) using staple drivers (not shown) but which may be similar to staple drivers (182) but arranged to correspond to staple cavities (226).

First staple forming pocket (446) of anvil (412) is configured to transition first legs (462*a*) of staples (430*a*) from first row (456) from the non-deformed state to the deformed state with the same firing stroke. Second staple forming pocket (448) of anvil (412) is configured to transition second legs (464*a*) of staples (430*a*) from first row (456) from the non-deformed state to the deformed state with the same firing stroke. Third staple forming pocket (449) of anvil (412) is configured to transition first legs (462*b*) of staples (430*b*) from second row (458) from the non-deformed state to the deformed state with the same firing stroke. Fourth staple forming pocket (451) of anvil (412) is configured to transition second legs (464*b*) of staples (430*b*) from second row (458) from the non-deformed state to the deformed state with the same firing stroke. In other words, a separate staple forming pocket (446, 448, 449, 451) deforms the same leg of each staple (430*a* or 430*b*) within the respective row. First and second staple forming pockets (446, 448) collective deform first and second legs (462*a*, 464*a*) of staples (430*a*). This may allow for legs to be bent to different degrees as will be described with reference to FIG. 16. First second, third and fourth staple forming pockets (446, 448, 449, 451) are shown in FIGS. 15A-15B as including gradually tapering portions (450). However, the shape of first second, third and fourth staple forming pockets (446, 448, 449, 451) may vary.

D. Fourth Exemplary Alternative Staple

Figure 16:
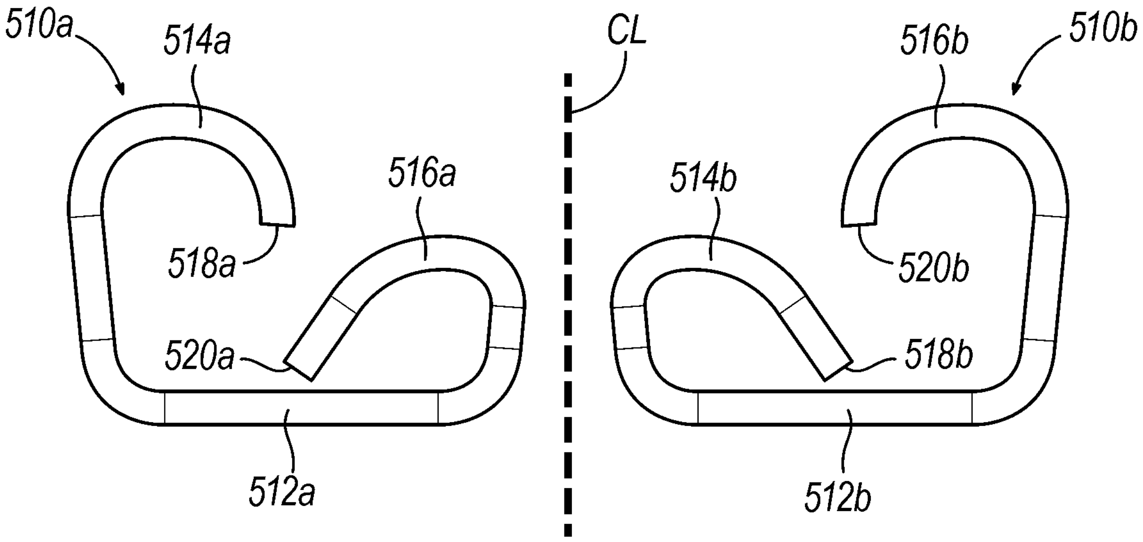
FIG. 16 depicts an elevation perspective view of fourth exemplary alternative staples.

FIG. 16 shows a perspective view of fourth exemplary alternative staples (510*a*-*b*) which may be formed using a staple cartridge (e.g., staple cartridge (210)) and an anvil (e.g., anvil (412, 612, 712, 810)). Staples (510*a*-*b*) each include a crown (512*a*-*b*) and first and second legs (514*a*-*b*, 516*a*-*b*). As shown, first legs (514*a*-*b*) include first terminal ends (518*a-b*). Similarly, second legs (516*a-b*) include second terminal ends (520*a-b*). In the deformed state, for first staple (510*a*), second terminal end (520*a*) is configured to be disposed closer to crown (512*a*) than first terminal end (518*a*). Similarly, for second staple (510*b*), first terminal end (518*b*) is configured to be disposed closer to crown (512*b*) than second terminal end (520*b*). In other words, staples (510*a-b*) in the deformed state have an intra-staple height difference between first and second legs (514*a-b*, 516*a-b*).

Staples (510*a-b*) may generally extend perpendicular to cut line (CL) to balance hemostasis and perfusion. Legs (514*b*, 516*a*) are disposed adjacent to cut line (CL) and provide for improved hemostasis given their close proximity to their respective crowns (512*a-b*). Legs (514*a*, 516*b*), disposed further away from cut line (CL), allow for perfusion given their spacing from their respective crown (512*a-b*). As a result, staples (510*a-b*) may perform multiple purposes including preventing blood flow right at cut line (CL) while still permitting some blood flow (i.e., perfusion) near cut line (CL). It may be beneficial to longitudinally offset legs (514*b*, 516*a*) or offset first and second terminal ends (518*a-b*, 520*a-b*) of legs (514*b*, 516*a*) relative to center of crown (512*a-b*) similar to staple (430*a-b*) to produce a three-dimensional staple. Staples (510*a-b*) may allow for greater perfusion to reduce a potential risk of necrosis. Using a continuous staple forming pocket (e.g., first second, third and fourth staple forming pockets (446, 448, 449, 451)) instead of individual staple forming pockets (e.g., individual staple-forming pockets (184*a*-184*b*) of anvil (72) for each staple (172) or staple forming pocket pairs (876) of anvil (860) for each staple (862)) removes a constraint on staple density that may otherwise be imposed by coining.

E. Third Exemplary Alternative Anvil

Figure 17:
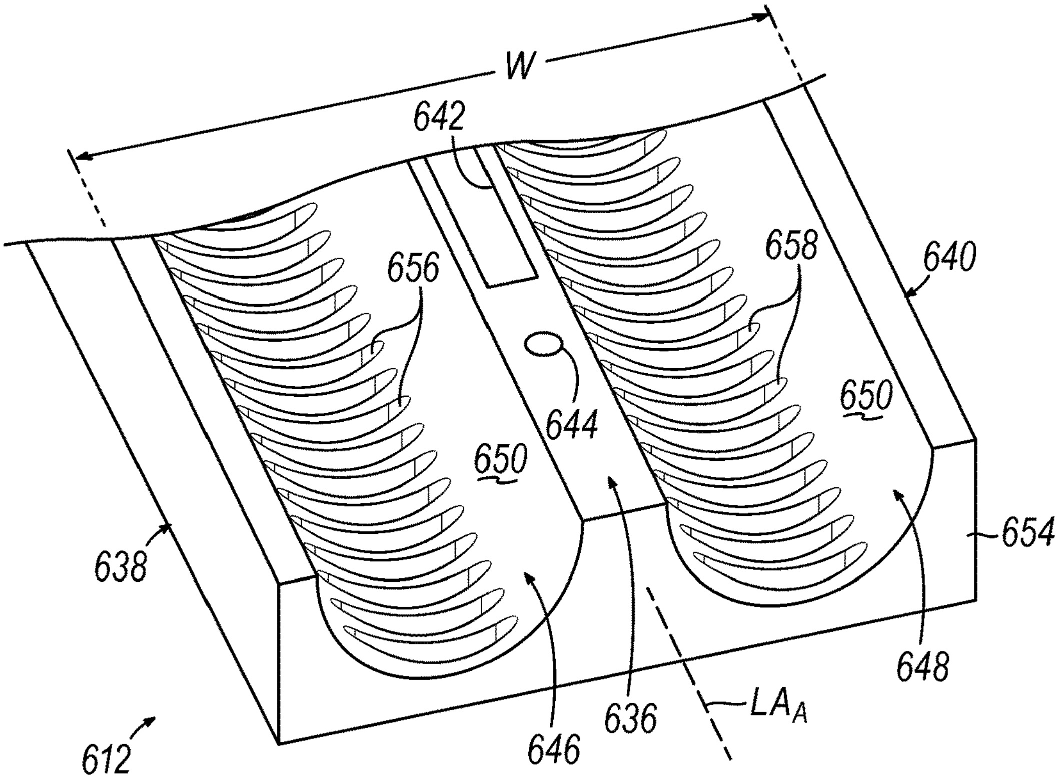
FIG. 17 depicts a partial perspective view of a third exemplary alternative anvil that includes first exemplary guide portions which may be incorporated into the stapler of FIG. 1.

FIG. 17 shows a partial perspective view of third exemplary alternative anvil (612) which may be incorporated into stapler (10) of FIG. 1 in place of anvil (72). While anvil (612) is described with reference to staple cartridge (210) and staples (230*a-b*), anvil (612) may be used with other staple cartridges and staples, including staple cartridge (310) and staples (330, 430*a*-430*b*, 510*a-b*, 838*a-b*, 910, 1010). Anvil (612) is similar to anvil (212). Anvil (612) is shown in the form of an anvil plate. Anvil (612) includes a distal connecting portion (636), a first lateral portion (638), and a second lateral portion (640). First and second lateral portions (638, 640) are separated by an elongate knife slot (642) that is configured to receive a knife member (184). Distal connecting portion (636) may include an aperture (not shown) to receive a pin to align anvil (612) with anvil half (14). Anvil (612) includes at least one staple forming pocket. As shown, anvil (612) includes first and second staple forming pockets (646, 648). First and second staple forming pockets (646, 648) extend continuously along a length of anvil (612) from a proximal end (not shown) of anvil (612) to a distal end (654) of anvil (612). In other words, first and second staple forming pockets (646, 648) include a continuous elongate channel extending parallel to longitudinal axis ($LA_A$) of anvil (612). First and second staple forming pockets (646, 648) extend parallel to one another and perpendicular to elongate knife slot (642). First and second staple forming pockets (646, 648) are shown as being generally semi-circular shape (650). Shapes of first and second staple forming pockets (646, 648) may vary. Anvil (612) is shown as being integrally formed together as a unitary piece.

Unlike first and second staple forming pockets (246, 248) that are shown as being generally smooth, first staple forming pocket (646) include includes a first guide feature (656) and second staple forming pocket (648) include includes a second guide feature (658). First guide feature (656) is configured to guide first and second legs (262*a*, 264*a*) of first staple (230*a*) from the non-deformed state to the deformed state with the same firing stroke. Second guide feature (658) is configured guide first and second legs (262*a*, 264*a*) of second staple (230*b*) from the non-deformed state to the deformed state with the same firing stroke. In other words, first guide feature (656) is configured to guide both first leg (262*a*) and second leg (264*a*). Similarly, second guide feature (656) is configured to guide both first leg (262*a*) and second leg (264*a*). First and second guide features (656, 658) are shown as being centrally disposed within first and second staple forming pockets (646, 648); however, this may vary. First and second guide features (656, 658) may allow for enhanced guidance of staple formation as surgical stapler is fired. First and second guide features (656, 658) may reduce the potential likelihood of staple tipping when staples (230*a-b*, 330, 510*a-b*, 838*a-b*, 910, 1010) move from the non-deformed state to the deformed state with the same firing stroke. While not shown, guide features (656, 658) may be applied to first, second, third, and fourth staple forming pockets (446, 448, 449, 451) shown and described above with reference to FIGS. 14-16.

F. Fourth Exemplary Alternative Anvil

Figure 18:
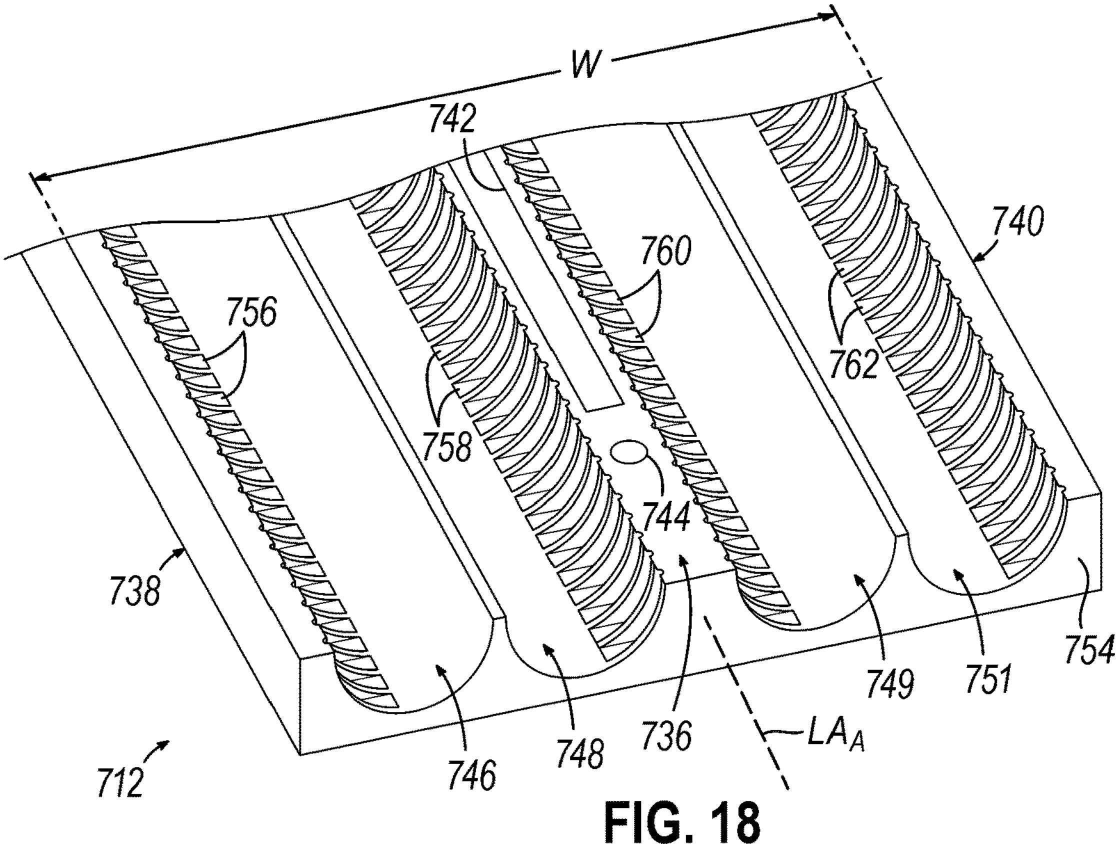
FIG. 18 depicts a partial perspective view of a fourth exemplary alternative anvil that includes second exemplary guide portions which may be incorporated into the stapler of FIG. 1.

FIG. 18 shows a partial perspective view of fourth exemplary alternative anvil (712) which may be incorporated into stapler (10) of FIG. 1 in place of anvil (72). While anvil (712) is described with reference to staple cartridge (210) and staples (230*a-b*), anvil (712) may be used with other staple cartridges and staples, including staple cartridge (310) and staples (330, 430*a*-430*b*, 510*a-b*, 838*a-b*, 910, 1010). Anvil (712) is similar to anvil (412), and is shown in the form of an anvil plate. Anvil (712) includes a distal connecting portion (736), a first lateral portion (738), and a second lateral portion (740). First and second lateral portions (738, 740) are separated by an elongate knife slot (742) that is configured to receive a knife member (184). Distal connecting portion (736) may include an aperture (not shown) to receive a pin to align anvil (712) with anvil half (14). Anvil (712) includes at least one staple forming pocket.

As shown, anvil (712) includes first, second, third, and fourth staple forming pockets (746, 748, 749, 751). First, second, third, and fourth staple forming pockets (746, 748, 749, 751) extend continuously along a length (L) of anvil (712) from a proximal end (not shown) of anvil (712) to a distal end (754) of anvil (712). In other words, first, second, third, and fourth staple forming pockets (746, 748, 749, 751) include a continuous elongate channel extending parallel to longitudinal axis ($LA_A$) of anvil (712). First, second, third, and fourth staple forming pockets (746, 748, 749, 751) extend parallel to one another and perpendicular to elongate knife slot (742). First, second, third, and fourth staple forming pockets (746, 748, 749, 751) are shown as being generally semi-circular shape (750). However, the shapes of first, second, third, and fourth staple forming pockets (746, 748, 749, 751) may vary. Anvil (712) is shown as being integrally formed together as a unitary piece.

While first, second, third, and fourth staple forming pockets (446, 448, 449, 451) are shown as being generally smooth, first staple forming pocket (746) include includes a first guide feature (756), second staple forming pocket (748)

include includes a second guide feature (758), third staple forming pocket (749) include includes a third guide feature (760), and fourth staple forming pocket (751) include includes a fourth guide feature (762). First guide feature (756) assists first staple forming pocket (746) of anvil (412) to transition first legs (262*a*) of staples (230*a*) from first row (256) from the non-deformed state to the deformed state with the same firing stroke. Second guide feature (758) assists second staple forming pocket (746) of anvil (712) to transition second legs (264*a*) of staples (230*a*) from first row (256) from the non-deformed state to the deformed state with the same firing stroke. Third guide feature (760) assists third staple forming pocket (749) of anvil (712) to transition first legs (262*b*) of staples (230*b*) from second row (258) from the non-deformed state to the deformed state with the same firing stroke.

First guide feature (762) assists fourth staple forming pocket (751) of anvil (712) to transition second legs (264*b*) of staples (230*b*) from second row (258) from the non-deformed state to the deformed state with the same firing stroke. In other words, a separate guide feature (756, 758, 760, 762) assists the same leg of each staples (230*a* or 230*b*) within the respective row. First, second, third, and fourth guide features (756, 758, 760, 762) may allow for enhanced guidance of staple formation as surgical stapler is fired. First, second, third, and fourth guide features (756, 758, 760, 762) may reduce potential likelihood of staple tipping when moving from the non-deformed state to the deformed state with the same firing stroke. While not shown, guide features (756, 758) may be applied to first and second staple forming pockets (246, 248) shown and described above with reference to FIGS. 7-8B.

Figure 19:
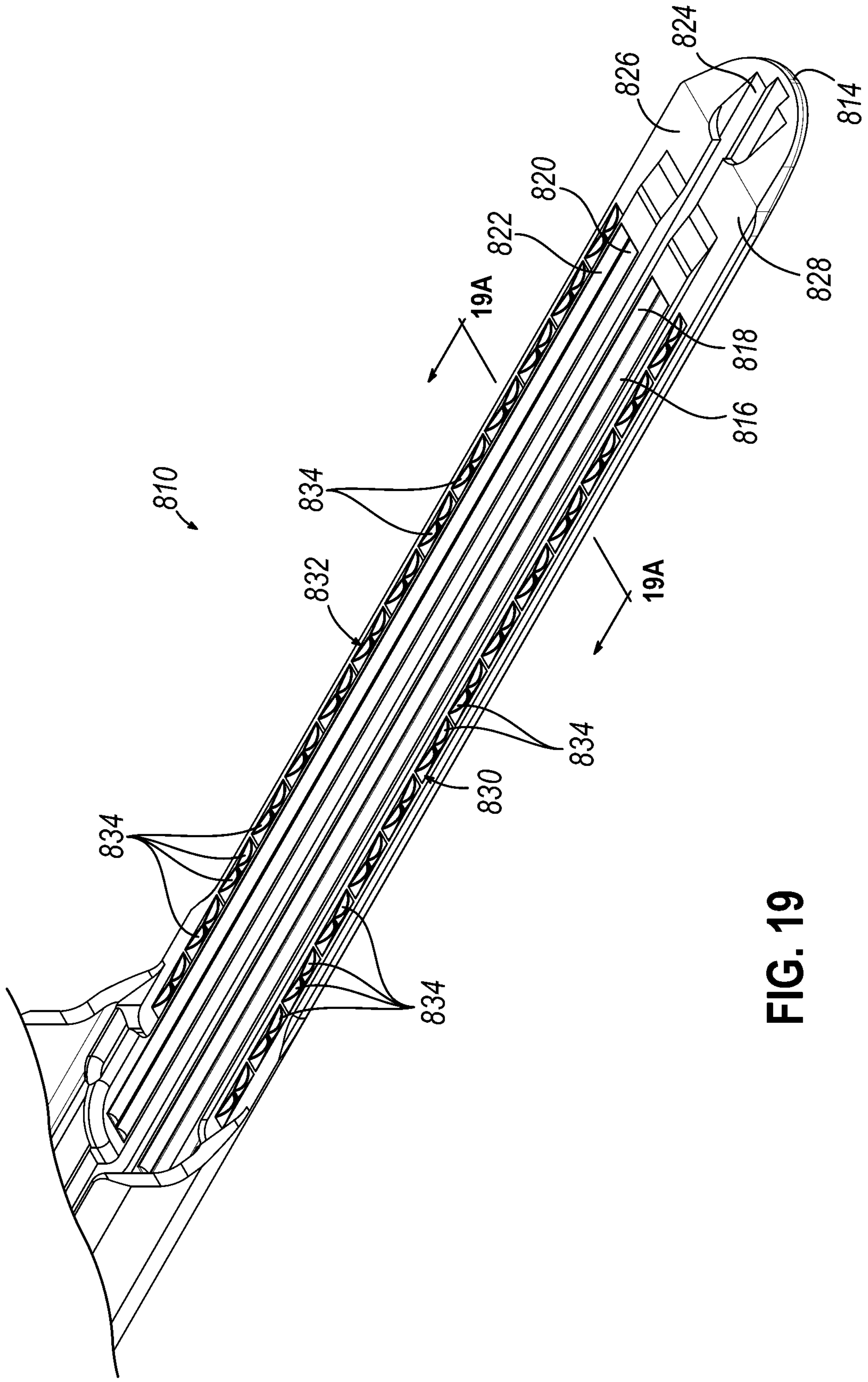
FIG. 19 depicts a partial perspective view of a fifth exemplary alternative anvil that includes second exemplary guide portions which may be incorporated into a surgical stapler.
Figure 19A:
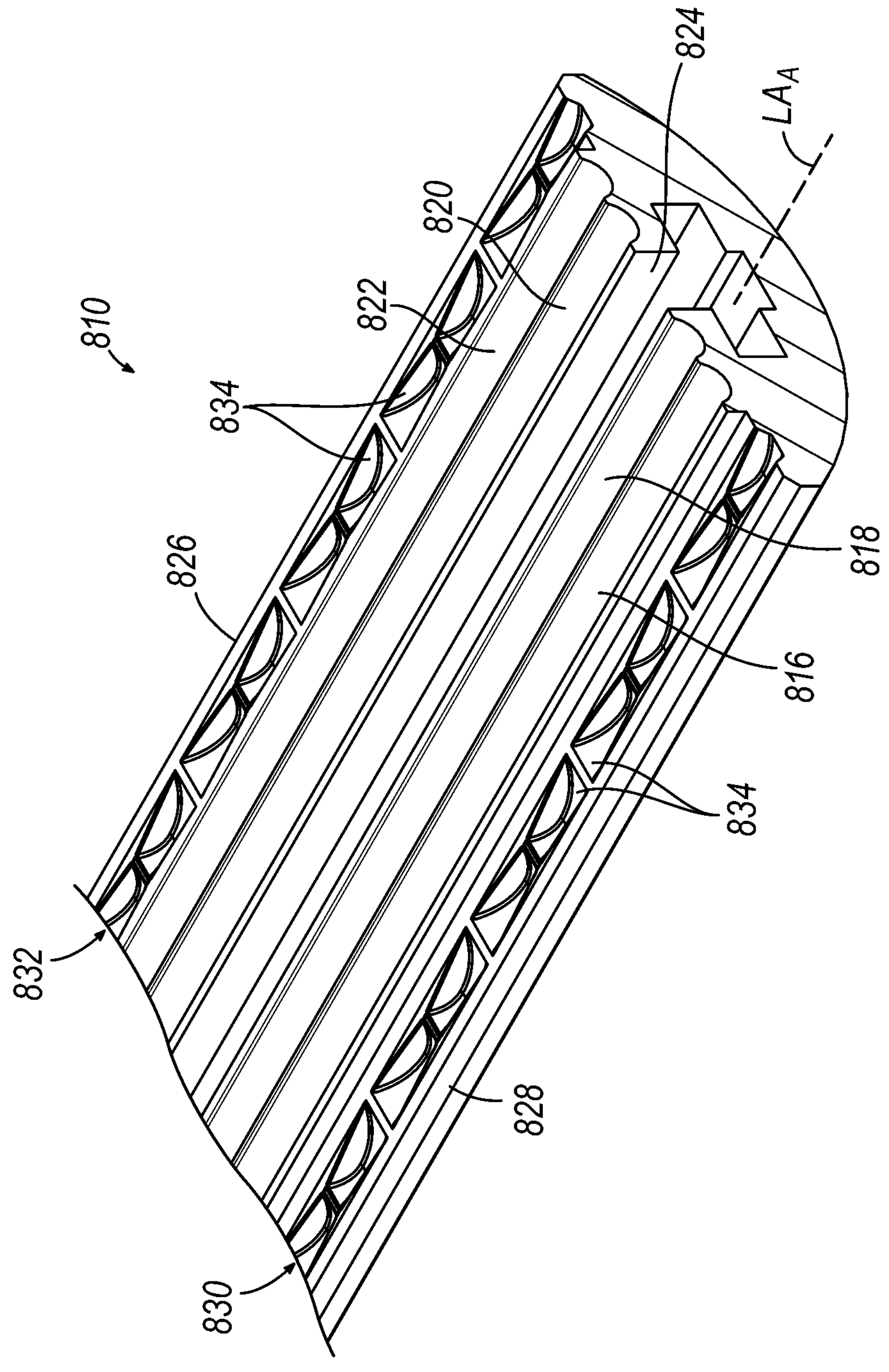
FIG. 19A depicts a partial perspective view of the anvil of FIG. 19 with a section taken along line 19A-19A of FIG. 19.
Figure 21:
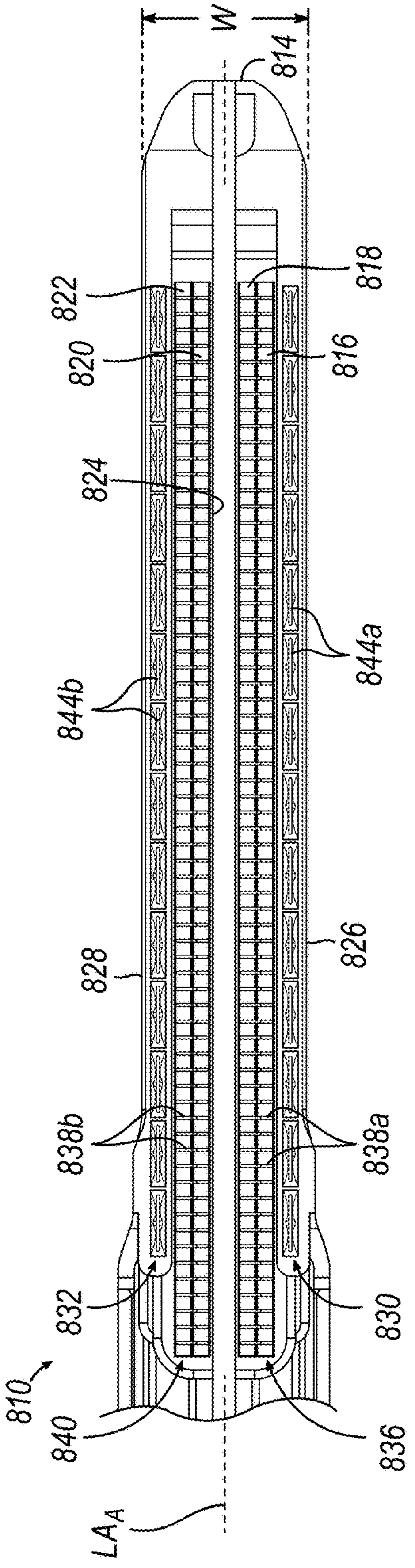
FIG. 21 depicts a partial top plan view of the anvil of FIG. 19 with a portion of the staples of FIG. 20 and sixth exemplary alternative staples in the deformed state.

G. Fifth and Sixth Exemplary Alternative Anvils and Fifth and Sixth Exemplary Alternative Staple FIGS. 19, 19A, 21, and 23 show a fifth exemplary alternative anvil (810). Anvil (810) is shown in the form of an anvil jaw of an end effector of an endocutter. For example, the teachings of this application may be combined with various exemplary endocutters, such that those shown and described in U.S. Pat. No. 9,517,065, entitled "Integrated Tissue Positioning and Jaw Alignment Features for Surgical Stapler," issued Dec. 13, 2016; U.S. Pat. No. 9,808,248, entitled "Installation Features for Surgical Instrument End Effector Cartridge," issued Nov. 7, 2017; and/or U.S. Pat. No. 10,092,292, entitled "Staple Forming Features for Surgical Stapling Instrument," issued Oct. 9, 2018, the disclosure of each which is incorporated by reference herein. While FIGS. 19, 19A, and 21 show anvil (810) in the form of an anvil jaw of an end effector of the endocutter, it is envisioned that the principles of anvil (810) described below may be used with other types of staplers, such as linear surgical staplers, circular surgical staplers, right angle surgical staplers, and curved surgical staplers, for example. For example, it is envisioned that the principles of anvil (810) may be combined with any one or more of anvils (212, 412, 612, 712) and used with staples (230*a*-*b*, 330, 430*a*-*b*, 510, 910, 1010) and/or staple cartridges (210, 310).

Anvil (810) includes proximal and distal ends (812, 814). Anvil (810) includes first, second, third and fourth staple forming pockets (816, 818, 820, 822) that extend parallel to one another and perpendicular to an elongate knife slot (824). First second, third and fourth staple forming pockets (816, 818, 820, 822) extend continuously along a length of anvil (810). First second, third and fourth staple forming pockets (816, 818, 820, 822) function similar to first second, third and fourth staple forming pockets (446, 448, 449, 451) described above with reference to FIGS. 14-15B. In other words, first second, third and fourth staple forming pockets (816, 818, 820, 822) are each formed as a continuous elongate channel extending parallel to longitudinal axis ($LA_A$) of anvil (810). First and second staple forming pockets (816, 818) are shown on a first side (826) of elongate knife slot (824), and third and fourth staple forming pockets (820, 822) are shown on a second side (828) of elongate knife slot (824). Shapes of first second, third and fourth staple forming pockets (816, 818, 820, 822) may vary. Anvil (810) also includes first and second outer rows (830, 832) of staple pocket pairs (834).

Figure 20:
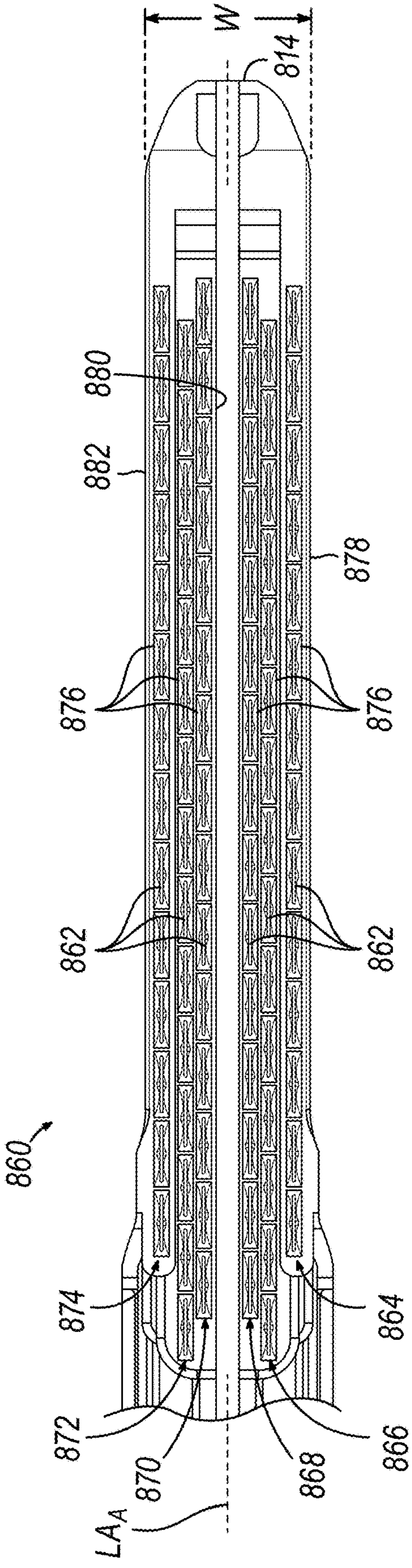
FIG. 20 depicts a partial top plan view of a sixth exemplary alternative anvil with fifth exemplary alternative staples in the deformed state.

FIG. 21 shows a partial top view of the anvil (810) of FIG. 19 with a portion of staples (838*a*-*b*) of FIG. 20 and sixth exemplary alternative staples (844*a*-*b*) in the deformed state. A first row (836) of staples (838*a*) is shown as being received by first and second staple forming pockets (816, 818). Similar to FIGS. 15A-15B regarding staples (430*a*), first and second legs (not shown) of staples (838*a*) are received by first and second staple forming pockets (816, 818) respectively. A second row (840) of staples (838*b*) is shown as being received by first and second rows (842, 846) of staple pocket pairs (834). Similar to FIGS. 15A-15B regarding staples (430*b*), first and second legs (not shown) of staples (838*b*) are received by third and fourth staple forming pockets (820, 822) respectively. While not shown, it is also envisioned that first and second staple forming pockets (246, 248) of anvil (212) may be used instead of first second, third and fourth staple forming pockets (816, 818, 820, 822). Anvil (810) is shown as being integrally formed together as a unitary piece. The firing assembly (100) includes a knife member that is configured to traverse through elongate knife slots (824, 880) to sever tissue of a patient along a cut line (CL). First outer row (830) of staple pocket pairs (834) may receive a first outer row (842) of staples (844*a*). Similarly, a second outer row (832) of staple pocket pairs (834) may receive a second outer row (846) of staples (844*b*).

Figure 22:
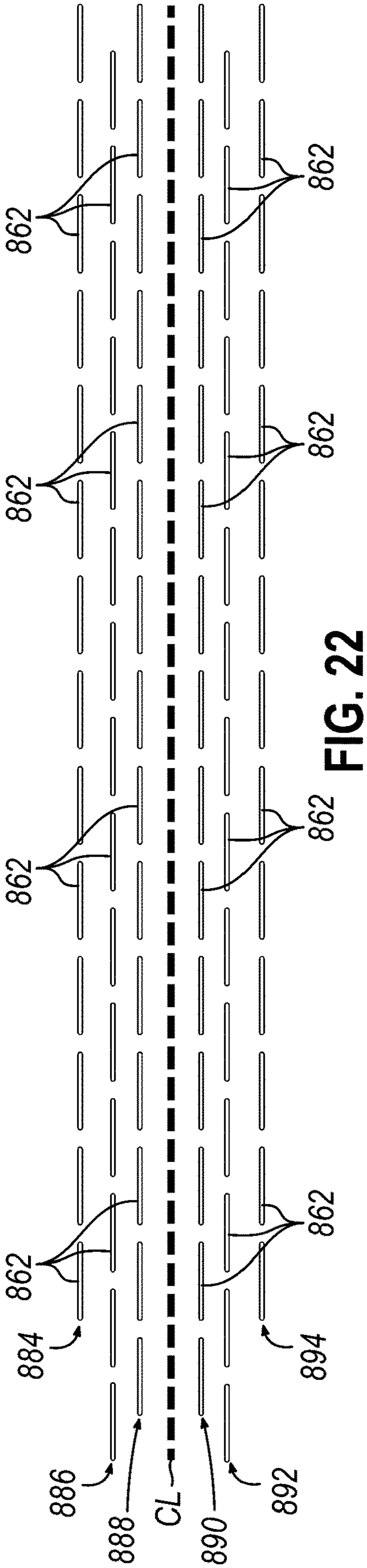
FIG. 22 depicts a top plan view of the arrangement of staples of FIG. 20.

FIG. 20 shows a partial top view of a sixth exemplary alternative anvil (860) with fifth exemplary alternative staples (862) in the deformed state, and FIG. 22 shows a top plan view of the arrangement of staples (862) of FIG. 20. Anvil (860) includes first, second, third, fourth, fifth, and sixth rows (864, 866, 868, 870, 872, 874) of staple forming pocket pairs (876). First, second, and third rows (864, 866, 868) are arranged on a first side (878) of an elongate knife slot (880). Fourth, fifth, and sixth rows (864, 866, 868) are arranged on a second side (882) of elongate knife slot (880). First, second, third, fourth, fifth, and sixth rows (864, 866, 868, 870, 872, 874) of staple forming pocket pairs (876) are configured to receive and deform first, second, third, fourth, fifth, and sixth rows (884, 886, 888, 890, 892, 894) of staples (862). First and sixth rows (864, 874) are generally similar in structure and positioning to first and second outer row (830, 832) of staple pocket pairs (834). As shown in FIGS. 20 and 22, staples (862) are oriented parallel to a cut line (CL) to provide hemostasis (i.e., prevent blood from passing through to cut line (CL)). This hemostasis is increased when two or more rows of staples (862) are staggered relative to each other as shown in FIG. 22. The arrangement of staples (862) of FIG. 22 oriented parallel with cut line (CL) does not maximize the number of staples (862) per inch along the length of cut line (CL).

Figure 23:
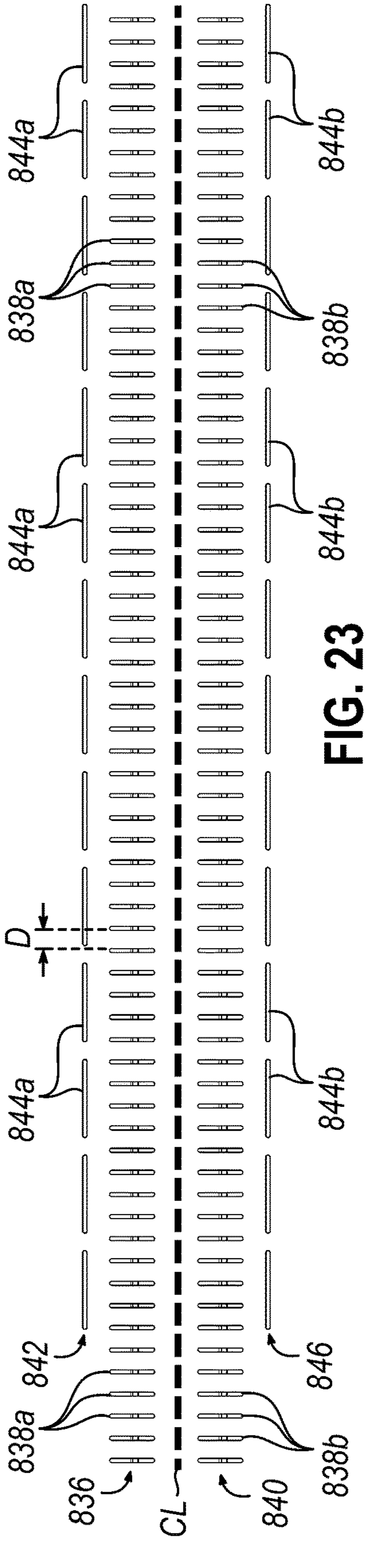
FIG. 23 depicts a top plan view of the arrangement of staples of FIG. 21.

FIG. 23 shows a top plan view of the arrangement of staples of FIG. 21. It is desirable to increase staple density without increasing a width (W) of anvil (810). FIG. 22 shows 88 staples (862), and FIG. 23 shows 160 staples (838*a-b*, 844*a-b*), which represents about an 82% increase in staples without increasing the footprint occupied by staples (230*a-b*). Comparing staples (862) of FIG. 22 with staples (838*a-b*, 844*a-b*) of FIG. 23, distance (D) between adjacent staples (838*a-b*) is reduced in FIG. 23. While FIG. 23 shows a particular arrangement of staples (838*a-b*, 844*a-b*); other suitable arrangements of staples (838*a-b*, 844*a-b*) are envisioned that may include more or fewer staples (838*a-b*, 844*a-b*). Anvil (810) of FIGS. 19, 19A, and 21 include staples (844*a-b*) extending parallel to elongate knife slot (824) and perpendicular to staples (838*a-b*).

A balance between hemostasis and perfusion may be desired. Allowing some perfusion reduces a potential risk of necrosis, as necrosis may result if blood flow to the tissue is completely cut off. However, it is desirable to have a degree of hemostasis so that tissue stops bleeding at cut line (CL). In other words, it may be desirable for cut tissue to receive blood, but not for the cut tissue to leak blood. Anvil (810) combines staples (838*a-b*) arranged perpendicular-to-cut-line with staples (844*a-b*) arranged parallel-with-cut-line. The balance of perfusion and hemostasis near cut line (CL) may be fine-tuned by adjusting the spacing (e.g., distance (D) (see FIG. 23)) between staples (838*a-b*) oriented perpendicular to cut line (CL). Perpendicular staples (e.g., staples (838*a-b*) may allow a minimal amount of perfusion while providing greater staple density along cut line (CL). Increased staple density along the length of cut line (CL) may provide enhanced structural integrity of the staple line. However, staples (844*a-b*) may affect magnitude of hemostasis performed by staples (838*a-b*). In other words, staples (838*a-b*) don't necessarily present a leak-through risk since that risk is mitigated by staples (844*a-b*).

H. Seventh Exemplary Alternative Staple

FIGS. 24-27 show a seventh exemplary alternative staple (910) that includes a crown (912) and first and second legs (914, 916). Crown (912) includes opposing first and second ends (918, 920). First leg (914) of staple (910) extends from first end (918) of crown (912). Second leg (916) of staple (910) extends from second end (920) of crown (912). First leg (914) includes a first terminal end (922). Similarly, second leg (916) includes a second terminal end (924). First and second terminal ends (922, 924) are shown as being pointed. Crown (912) may be generally rectangular when omitting first and second tapered portions (926, 928). Crown (912) has a first cross-sectional area. The first cross-sectional area is the same as first surface (930) of crown (912). The first cross-sectional area of crown (912) may allow for greater control by staple driver (not shown), but which may be similar to staple driver (182). Staple driver (182) may be modified so as to have a wider recess portion to accommodate width (W) (see FIG. 27) of crown (912). In some versions, first and second legs (914, 916) each have a second cross-sectional area that is less than the first cross-sectional area of crown (912). Staple (910) may be stamped from sheet metal with first and second legs (914, 916) offset then bent to the non-deformed state for insertion into a staple cartridge.

Figure 24:
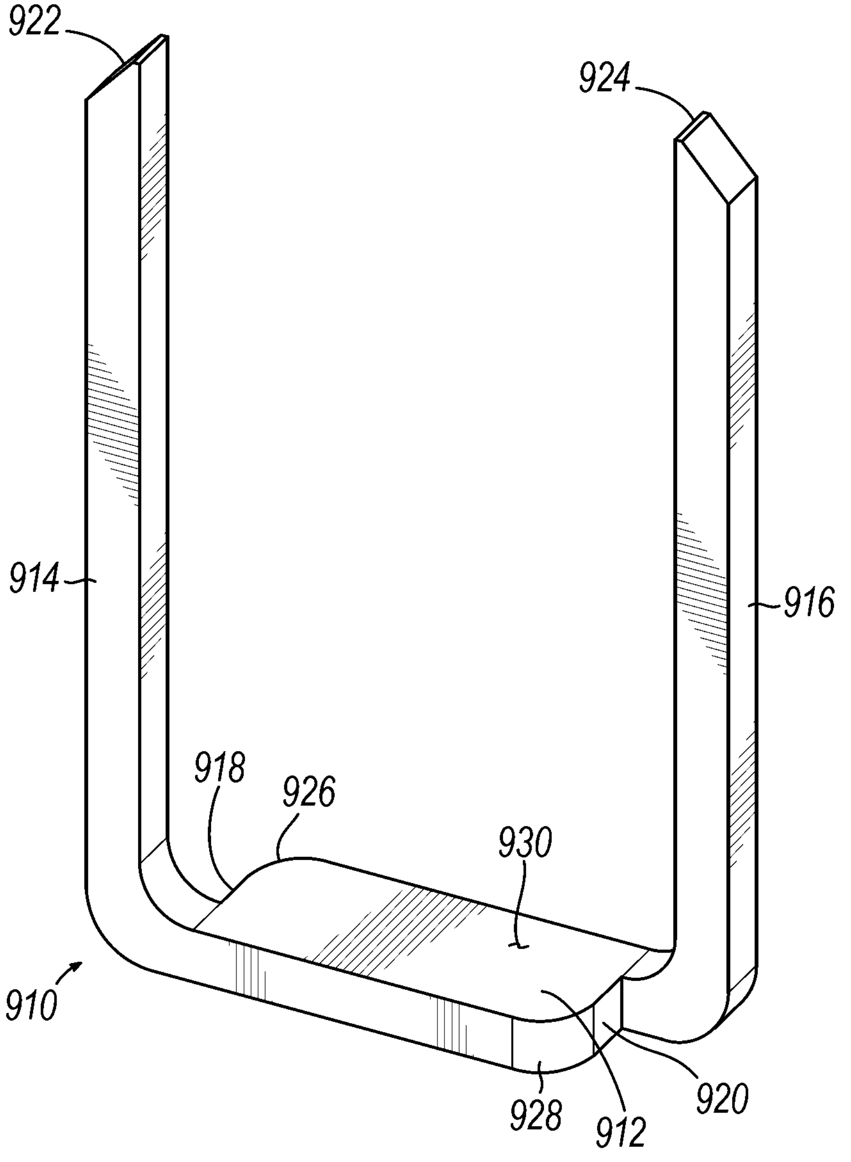
FIG. 24 depicts a perspective view of a seventh exemplary alternative staple.
Figure 25B:
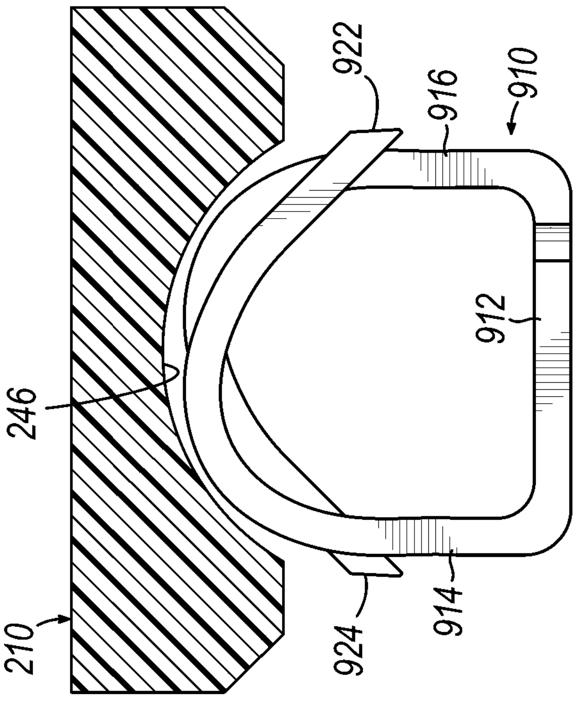
FIG. 25B depicts a schematic sectional view of the staple and the anvil of FIG. 25A, but with the staple in a deformed state.
Figure 25A:
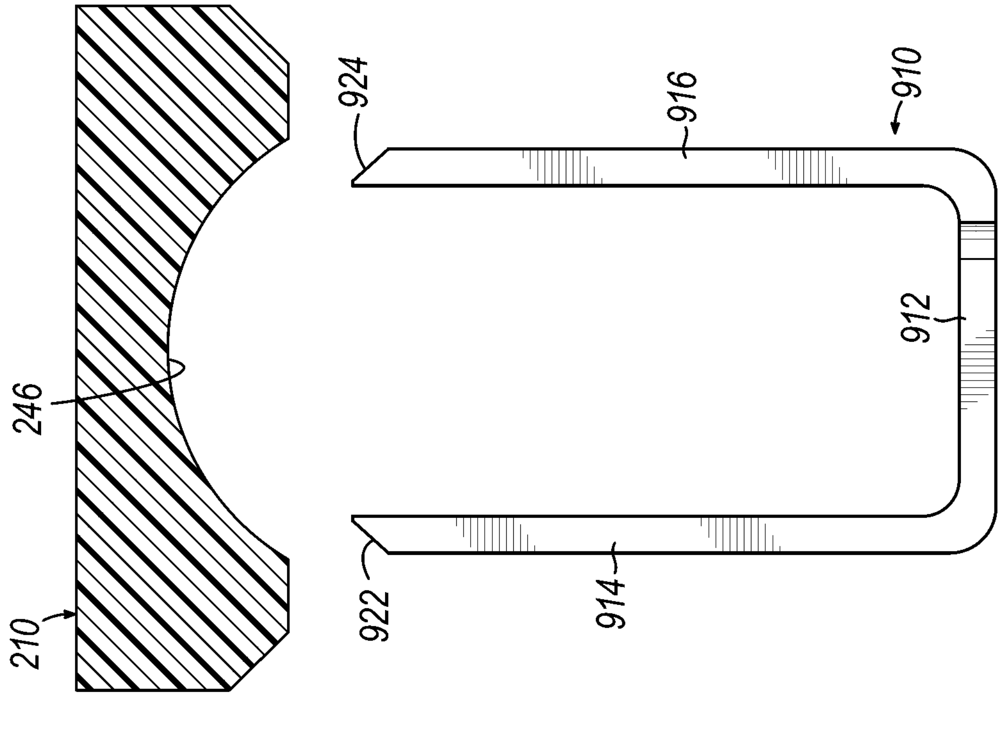
FIG. 25A depicts a schematic sectional view of the staple of FIG. 24 in a non-deformed state prior to contacting a staple forming pocket of the anvil of FIG. 7.
Figure 26:
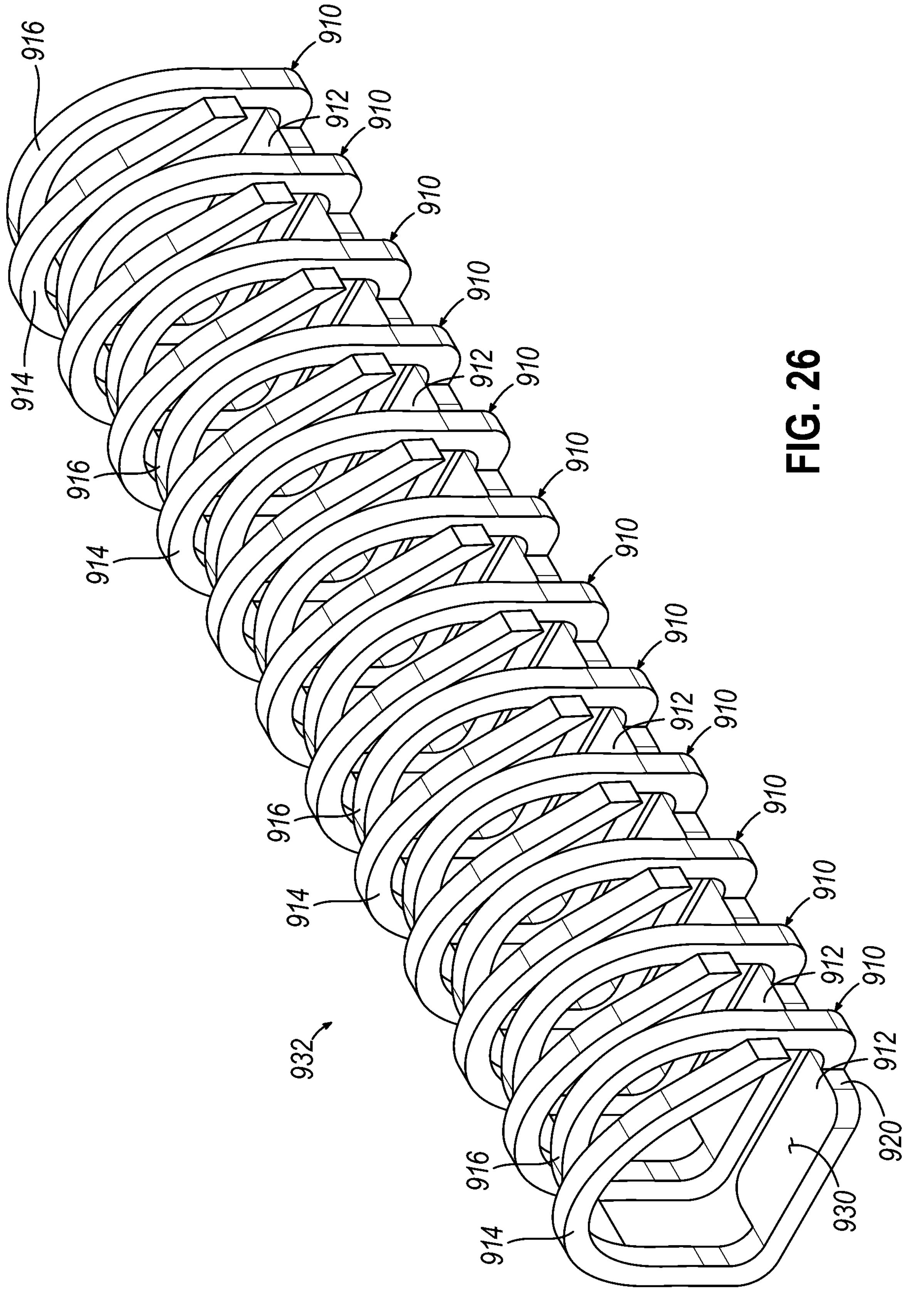
FIG. 26 depicts a perspective view of an arrangement of staples of FIG. 24 but in the deformed state of FIG. 25B.
Figure 27:
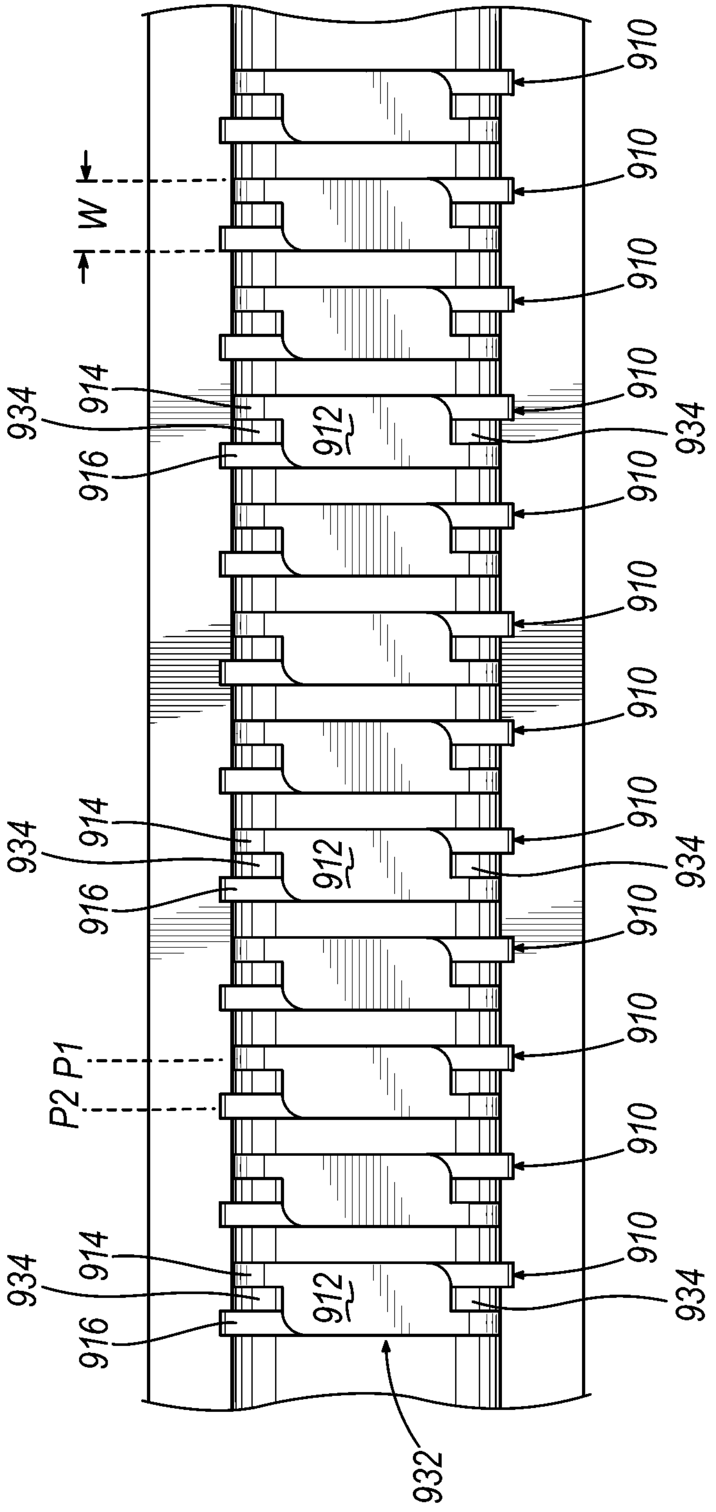
FIG. 27 depicts a bottom view of the arrangement of staples of FIG. 26 deformed against the staple forming pocket of the anvil of FIG. 25B.

FIG. 25A shows a schematic sectional view of staple (910) of FIG. 24 in a non-deformed state prior to contacting staple forming pocket (246) of anvil (212). Staple (910) may be combined with other alternative staple forming pockets including staple forming pockets (248, 446, 448, 449, 451, 646, 648, 746, 748, 749, 751). As shown in FIG. 25A, first and second legs (914, 916) may be formed generally perpendicular to the axis of staple forming pocket (246) of anvil (212). FIG. 25B shows a schematic sectional view of staple (910) and staple forming pocket (246) of anvil (212) of FIG. 25A, but with staple (910) in the deformed state after being deformed by staple forming pocket (246). FIGS. 26-27 show an arrangement (932) of staples (910) in the deformed state. In the non-deformed state shown in FIG. 24 and the deformed state shown in FIG. 27, first leg (914) is offset from second leg (916) such that a gap (934) exists between first and second legs (914, 916). First and second legs (914, 916) extend in different planes (i.e., are not co-planar) in each of the non-deformed or deformed states. As shown in FIG. 27, first leg (914) extends along a first plane (P1) and second leg (916) extends along a second plane (P2). Staple (910) may minimize the potential risk of staple tipping when being formed in staple forming pockets (446, 448, 449, 451, 646, 648, 746, 748, 749, 751) which are shown as extending continuously.

I. Eighth Exemplary Alternative Staples

Figure 28:
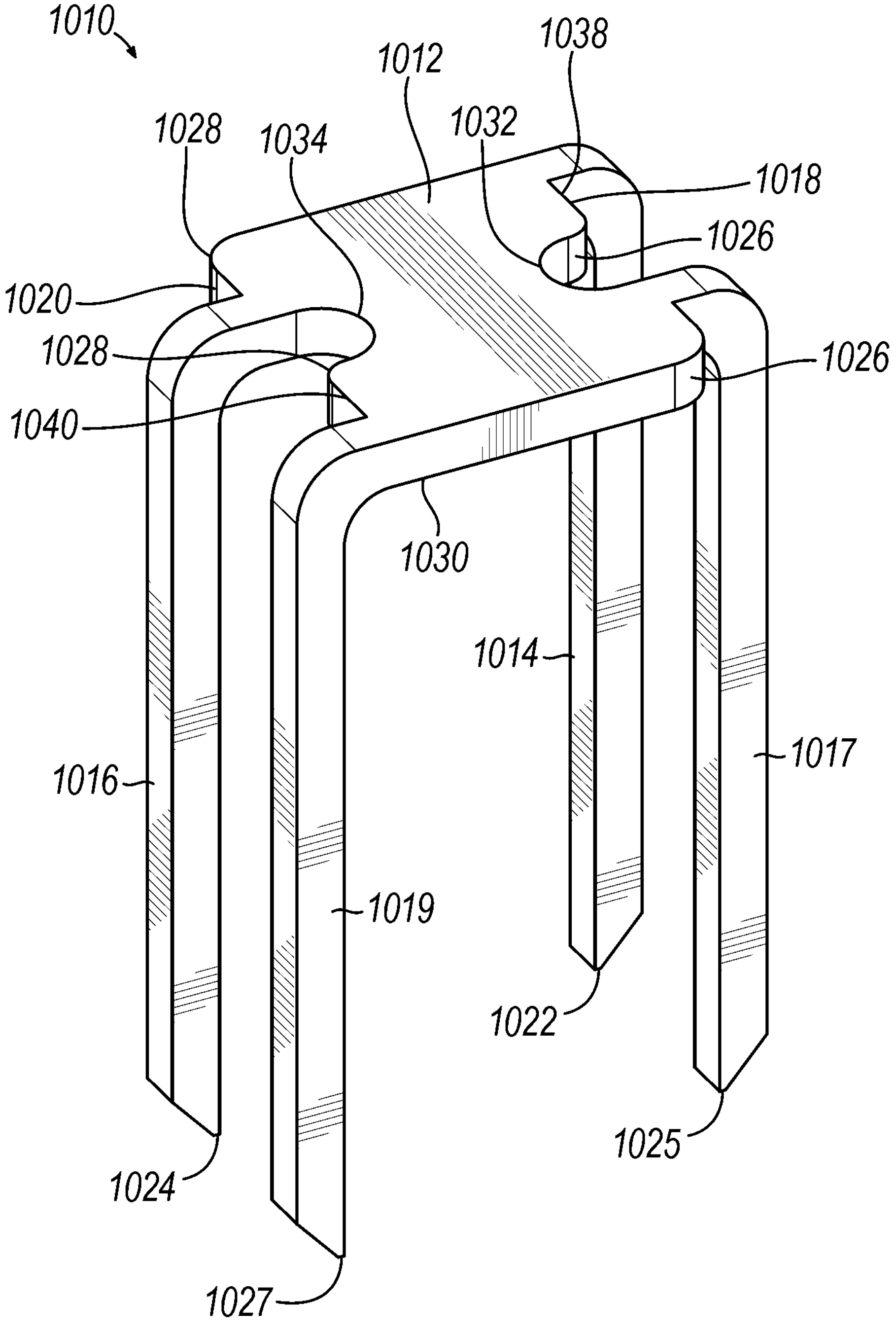
FIG. 28 depicts a perspective view of an eighth exemplary alternative staple.
Figure 29A:
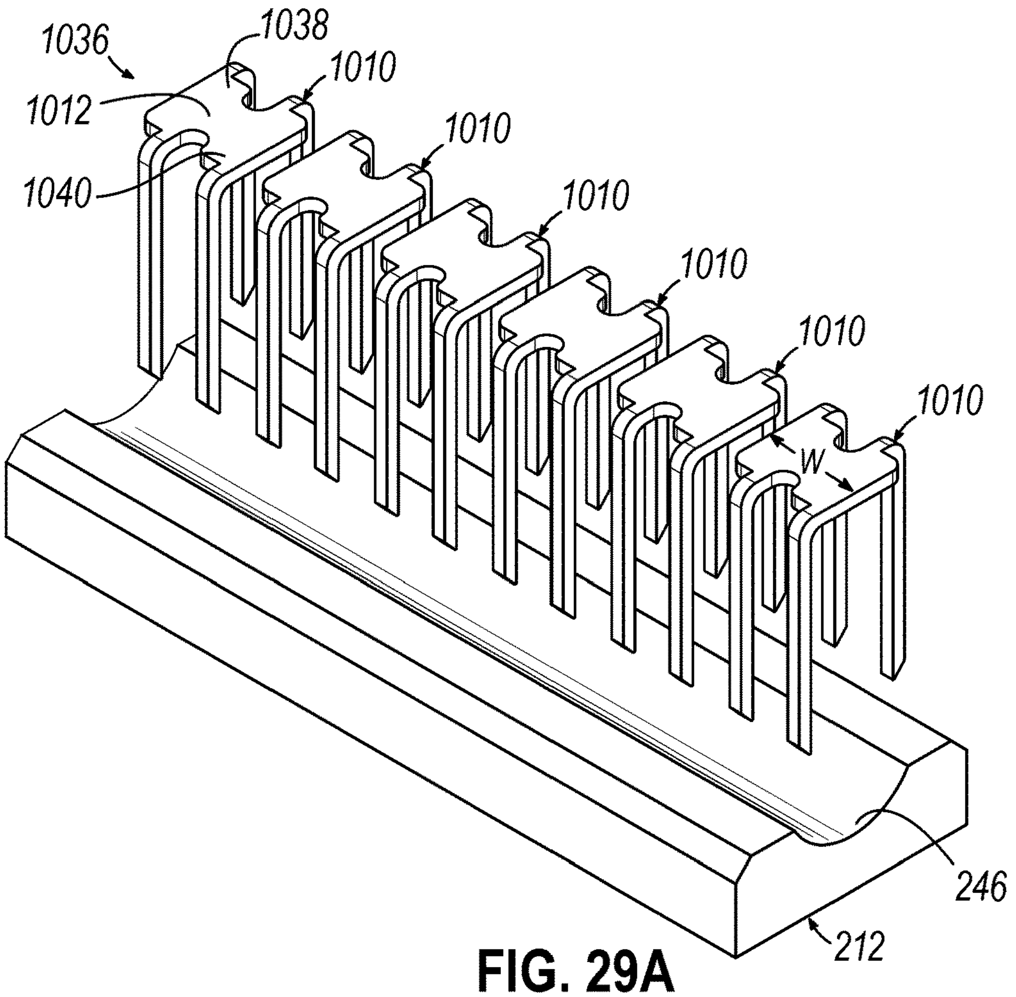
FIG. 29A depicts a schematic perspective view of the staples of FIG. 28 in a non-deformed state prior to contacting a staple forming pocket of the anvil of FIG. 7.
Figure 29B:
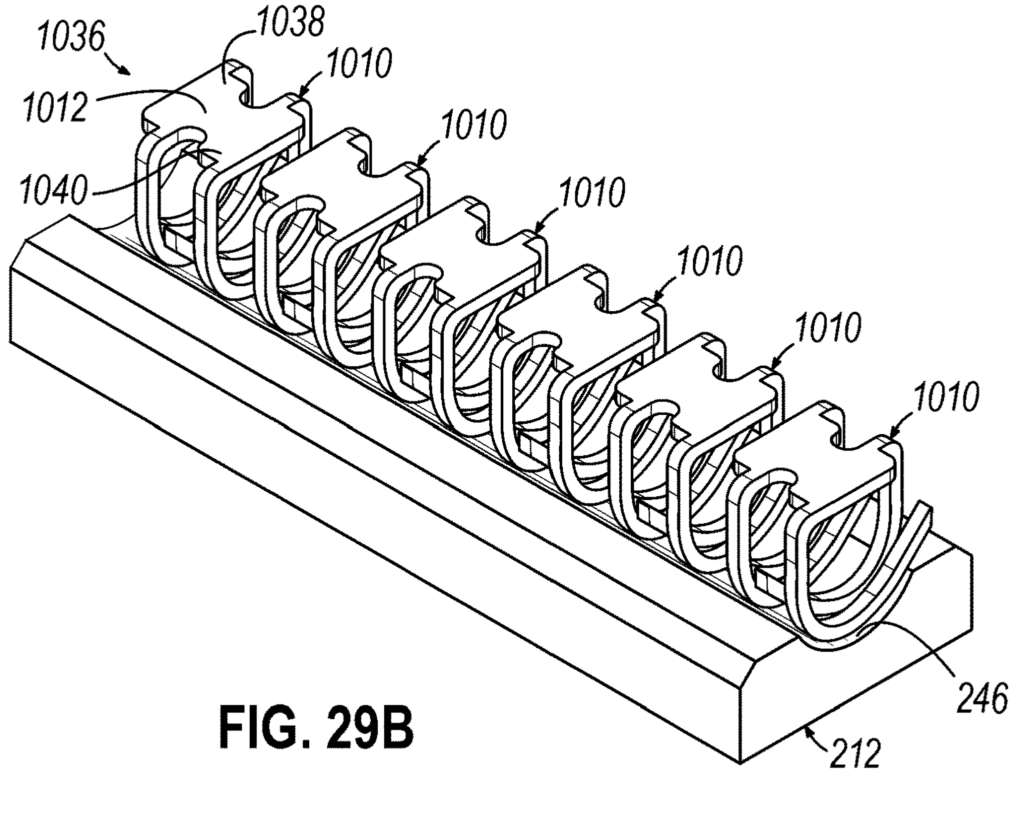
FIG. 29B depicts a schematic perspective view of the staples and the anvil of FIG. 29A, but with the staples in a deformed state.

FIGS. 28-29B show an eighth exemplary alternative staple (1010) that includes a crown (1012) and a plurality of legs. Unlike staple (910) that includes first and second legs (914, 916), staple (1010) includes first, second, third, and fourth legs (1014, 1016, 1017, 1019). Crown (1012) includes opposing first and second ends (1018, 1020). First and third legs (1014, 1017) of staple (1010) extend from first end (1018) of crown (1012). Second and fourth legs (1016, 1019) of staple (1010) extend from second end (1020) of crown (1012). First leg (1014) includes a first terminal end (1022), second leg (1016) includes a second terminal end (1024), third leg (1016) includes a third terminal end (1024), and fourth leg (1016) includes a fourth terminal end (1024). First leg (1014) is shown as being offset from second leg (1016), such that first and second legs (1014, 1016) do not extend along a common plane. Similarly, third leg (1017) is shown as being offset from fourth leg (1019), such that third and fourth legs (1017, 1019) do not extend along a common plane. However, in some versions, first and second legs (1014, 1016) may extend from a common plane and third and fourth legs (1017, 1019) may extend from a common plane.

First, second, third, and fourth terminal ends (1022, 1024, 1025, 1027) are shown as being pointed. First leg (1014) is offset from second leg (1016) such that first and second legs (1014, 1016) extend in different planes (i.e., are not co-planar) in each of the non-deformed or deformed states. First leg (1014) extends along a first plane and second leg (1016) extends along a second plane similar to staple (910). Crown (1012) may be generally rectangular, with or without first and second tapered portions (1026, 1028). Crown (1012) has a first cross-sectional area that may allow for greater control by staple driver (not shown), but which may be similar to staple driver (182). Staple driver (182) may be modified to have a wider contact portion to accommodate the increased width (W) (see FIG. 29A) of crown (1012). In some versions, first, second, third, and fourth legs (1014, 1016, 1017, 1019) each have a second cross-sectional area that is less than the first cross-sectional area of crown (1012). Staple (1010) may be stamped from sheet metal with first and second legs (1014, 1016) offset then bent to the non-deformed state for insertion into a staple cartridge. Unlike staple (910), crown (1012) includes a first notch (1042) disposed between first and third legs (1014, 1017) and a second notch (1044) disposed between second and fourth legs (1016, 1019). First and second notches (1042, 1044) of crown (1012) may mate with complementary features of a staple driver (not shown) but which may be similar to staple driver (182) further promote stability/alignment during formation. In some versions, first and second notches (1042, 1044) may be omitted.

FIGS. 29A-29B show an arrangement (1036) of staples (1010). FIG. 29A shows a schematic sectional view of arrangement (1036) of staples (1010) of FIG. 28 in a non-deformed state prior to contacting staple forming pocket (246) of anvil (212), and FIG. 29B shows a schematic sectional view with arrangement (1036) of staples (1010) in a deformed state after being deformed by staple forming pocket (246). Staple (910) may be used in conjunction with other alternative staple forming pockets including staple forming pockets (248, 446, 448, 449, 451, 646, 648, 746, 748, 749, 751, 816, 818, 820, 822). As shown, first, second, third, and fourth legs (1014, 1016, 1017, 1019) may be formed generally perpendicular to axis of staple forming pocket (246) of anvil (212). First leg (1014) is offset from second leg (1016) such that a gap (1038) exists between first and second legs (1014, 1016). Similarly, third leg (1017) is offset from fourth leg (1019) such that a gap (1040) exists between first and second legs (1014, 1016). Staple (1010) may minimize a potential risk of staple tipping when being formed in staple forming pockets (446, 448, 449, 451, 646, 648, 746, 748, 749, 751, 816, 818, 820, 822) which are shown as extending continuously.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a stapling assembly that includes first and second staples, wherein each of the first and second staples include a first leg; and (b) an anvil that together with the stapling assembly is configured to clamp tissue of a patient, wherein the anvil includes a first staple forming pocket that is configured to transition the first legs of the first and second staples from a non-deformed state to a deformed state with the same firing stroke.

Example 2

The apparatus of Example 1, wherein the first staple forming pocket comprises an elongate continuous channel extending parallel to a longitudinal axis of the anvil.

Example 3

The apparatus of Example 2, wherein the first staple forming pocket includes first and second guide features disposed within the elongate continuous channel, wherein the first guide feature is configured to guide the first leg of the first staple from the non-deformed state to the deformed state with the same firing stroke, wherein the second guide feature is configured guide the first leg of the second staple from the non-deformed state to the deformed state with the same firing stroke.

Example 4

The apparatus of any one or more of the preceding Examples, wherein the stapling assembly includes an elongate knife slot, wherein the apparatus further comprises a knife member configured to traverse through the elongate knife slot to sever the tissue of the patient, wherein the first staple forming pocket extends parallel to the elongate knife slot.

Example 5

The apparatus of Example 4, wherein the apparatus is movable between an open configuration to receive the tissue between the stapling assembly and the anvil and a closed configuration to clamp the tissue between the stapling assembly and the anvil, the apparatus further comprising a firing assembly that includes the knife member, wherein actuation of the firing assembly is configured to cut the tissue using the knife member and staple the tissue using the first and second staples.

Example 6

The apparatus of any one or more of Examples 4 through 5, wherein the first and second staples each further include second legs, wherein the stapling assembly includes first and second staple cavities configured to receive the respective first and second staples, wherein the first and second staple cavities are obliquely oriented relative to the elongate knife slot so as to angle the first and second legs of the first and second staples in a three-dimensional orientation in the deformed state.

Example 7

The apparatus of any one or more of Examples 4 through 6, further comprising a third staple configured to extend perpendicular to the elongate knife slot.

Example 8

The apparatus of any one or more of Examples 4 through 5, further comprising a third staple extending parallel to the elongate knife slot and perpendicular to the first and second staples.

Example 9

The apparatus of any one or more of Examples 1 through 5 and Examples 7 through 8, wherein the first and second staples each include second legs, wherein the anvil includes a second staple forming pocket configured to transition the second legs of the first and second staples from a non-deformed state to a deformed state with the same firing stroke.

Example 10

The apparatus of any one or more of Examples 1 through 5 and Examples 7 through 8, wherein the first and second staples each include second legs, wherein the first staple forming pocket is configured to transition the first and second legs of the first and second staples from the non-deformed state to the deformed state with the same firing stroke.

Example 11

The apparatus of any one or more of Examples 1 through 6 and Examples 9 through 10, the stapling assembly further comprising third and fourth staples, wherein the third and fourth staples each include first legs, wherein the first staple forming pocket is configured to transition the first legs of the first, second, third, and fourth staples from the non-deformed state to the deformed state with the same firing stroke.

Example 12

The apparatus of Example 11, wherein the stapling assembly extends along a longitudinal axis, wherein the first, second, third, and fourth staples each extend perpendicular to the longitudinal axis of the stapling assembly.

Example 13

The apparatus of any one or more of Examples 1 through 12, wherein the first staple further comprising a second leg and a first crown that includes opposing first and second ends, wherein the first leg of the first staple extends from the first end of the first crown, wherein the second leg of the first staple extends from the second end of the first crown.

Example 14

The apparatus of Example 13, wherein the first crown includes a first notch disposed between the first and third legs of the first staple.

Example 15

The apparatus of any one or more of Examples 13 through 14, the first staple comprising: (i) a third leg extending from the first end of the first crown and spaced apart from the first leg, and (ii) a fourth leg extending from the second end of the first crown and spaced apart from the second leg.

Example 16

The apparatus of any one or more of Examples 13 through 15, wherein the first leg includes a first terminal end, wherein the second leg includes a second terminal end, wherein the second terminal end is configured to extend closer from the first crown than the first terminal end in the deformed state.

Example 17

The apparatus of any one or more of Examples 13 through 16, wherein the first leg extends along a first plane, wherein the second leg extends along a second plane, wherein the second plane is offset from the first plane.

Example 18

The apparatus of any one or more of Examples 13 through 17, wherein the first leg of the first staple is offset from the second leg such that the first and second legs of the first staple are not co-planar in either the non-deformed or deformed states.

Example 19

An apparatus comprising: (a) a stapling assembly that includes first and second staples, wherein each of the first and second staples include first and second legs, wherein the first leg, wherein the second leg wherein the first leg of the first staple extends along a first plane, wherein the second leg of the first staple extends along a second plane that is offset from the first plane in a non-deformed state and a deformed state; and (b) an anvil that together with the stapling assembly is configured to clamp tissue of a patient, wherein the anvil includes a first staple forming pocket that is configured to transition at least the first legs of the first and second staples from the non-deformed state to the deformed state with the same firing stroke.

Example 20

The apparatus of Example 19, wherein the first staple includes a first crown, wherein the first crown has a first cross-sectional area, wherein the first and second legs each have a second cross-sectional area that is less than the first cross-sectional area.

Example 21

The apparatus of any one or more of Examples 19 through 20, wherein the first staple forming pocket comprises an elongate continuous channel extending parallel to a longitudinal axis of the anvil, wherein the elongate continuous channel is configured to transition the first legs of the first and second staples at a non-zero angle relative to the longitudinal axis of the anvil in the deformed state.

Example 22

A method of operating a surgical stapling instrument comprising: actuating a stapling assembly of the surgical stapling instrument to drive first legs of first and second staples through tissue of a patient from a non-deformed state to a deformed state using the same staple forming pocket.

Example 23

The method of Example 22, wherein the first and second staples include second legs, wherein actuating the stapling assembly further comprises actuating the stapling assembly to drive the first and second legs of the first and second staples through the tissue of the patient from the non-deformed state to the deformed state using same staple forming pocket.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:

(a) a stapling assembly that includes first, second, third, and fourth discrete staples, wherein each of the first, second, third, and fourth discrete staples includes first and second legs; and (b) an anvil that together with the stapling assembly is configured to clamp tissue of a patient, the anvil comprising:

(i) a first staple forming pocket that is configured to sequentially transition the first legs of the first and second discrete staples from a non-deformed state to a deformed state with the same firing stroke, and (ii) a second staple forming pocket that is configured to transition the second legs of the first and second discrete staples from a non-deformed state to a deformed state, (iii) a first staple forming pocket pair configured to sequentially transition the first and second legs of the third discrete staple from a non-deformed state to a deformed state, and (iv) a second staple forming pocket pair configured to sequentially transition the first and second legs of the fourth discrete staple from a non-deformed state to a deformed state after the first staple forming pocket pair transitions the first and second legs of the third discrete staple from the non-deformed state to the deformed state with the same firing stroke, wherein the first and second staple forming pockets are arranged and configured to cause the first and second discrete staples to have a greater staple density than the third and fourth discrete staples in the deformed state.

2. The apparatus of claim 1, wherein the stapling assembly includes fifth and sixth discrete staples, wherein each of the fifth and sixth discrete staples includes a first leg, wherein the anvil further comprises a third staple forming pocket that is configured to sequentially transition the first legs of the fifth and sixth discrete staples from a non-deformed state to a deformed state with the same firing stroke.

3. The apparatus of claim 2, wherein the anvil includes an elongate knife slot, wherein the elongate knife slot is interposed between the first and third staple forming pockets, wherein the first and second staple forming pockets are positioned between the elongate knife slot and the first and second staple forming pocket pairs.

4. The apparatus of claim 3, wherein the first and third staple forming pockets extend parallel to and adjacent the elongate knife slot.

5. The apparatus of claim 3, wherein each of the first, second, fifth and sixth discrete staples extends perpendicular to the elongate knife slot.

6. The apparatus of claim 2, wherein each of the fifth and sixth discrete staples includes a second leg, wherein the anvil further comprises a fifth staple forming pocket that is configured to sequentially transition the second legs of the fifth and sixth discrete staples from a non-deformed state to a deformed state with the same firing stroke.

7. The apparatus of claim 1, wherein the first, second, third, and fourth discrete staples are spaced apart in the non-deformed and deformed states.

8. The apparatus of claim 1, wherein the first and second discrete staples are smaller than the third and fourth discrete staples.

9. An apparatus comprising:

(a) a stapling assembly that includes first, second, third, fourth, fifth and sixth discrete staples, wherein each of the first, second, third, and third, fourth, fifth and sixth discrete staples includes a first leg; and (b) an anvil that together with the stapling assembly is configured to clamp tissue of a patient, the anvil comprising:

(i) a first staple forming pocket that is configured to sequentially transition the first legs of the first and second discrete staples from a non-deformed state to a deformed state with the same firing stroke, (ii) a second staple forming pocket that is configured to sequentially transition the first legs of the third and fourth discrete staples from a non-deformed state to a deformed state with the same firing stroke, (iii) a third staple forming pocket configured to transition the first leg of the fifth discrete staple from a non-deformed state to a deformed state, and (iv) a fourth staple forming pocket configured to transition the first leg of the sixth discrete staple from a non-deformed state to a deformed state after the third staple forming pocket transitions the first leg of the fifth discrete staple from the non-deformed state to the deformed state, wherein the first and second staple forming pockets are arranged and configured to cause the first, second, third, and fourth discrete staples to have a greater staple density than the fifth and sixth discrete staples in the deformed state.

10. The apparatus of claim 9, wherein the anvil includes an elongate knife slot, wherein the apparatus further comprises a knife configured to traverse through the elongate knife slot to sever the tissue of the patient, wherein the first and second staple forming pockets extend parallel to and are offset from the elongate knife slot, wherein the first staple forming pocket is positioned between the elongate knife slot and the third and fourth staple forming pockets.

11. The apparatus of claim 9, wherein each of the first and second discrete staples includes a second leg, further comprising a fifth staple forming pocket that is configured to sequentially transition the second legs of the first and second discrete staples from a non-deformed state to a deformed state with the same firing stroke.

12. The apparatus of claim 11, wherein each of the third and fourth discrete staples includes a second leg, further comprising a sixth staple forming pocket that is configured to sequentially transition the second legs of the third and fourth discrete staples from a non-deformed state to a deformed state with the same firing stroke.

13. The apparatus of claim 9, the anvil further comprising:

(a) a first lateral side, (b) a second lateral side disposed opposite to the first lateral side, and (c) a longitudinally extending row of staple forming pocket pairs configured to sequentially transition legs of staples of the stapling assembly from a non-deformed state to a deformed state with the same firing stroke, wherein the longitudinal row of staple forming pocket pairs extends longitudinally between the first lateral side and the second staple forming pocket.

14. The apparatus of claim 9, further comprising an elongate knife slot extending along a longitudinal axis of the anvil, wherein the first staple forming pocket is positioned on a first side of the elongate knife slot, wherein second first staple forming pocket is positioned on a second side of the elongate knife slot opposite the first side.

15. The apparatus of claim 9, wherein the first, second, third, and fourth discrete staples are smaller than the fifth and sixth discrete staples.

16. An apparatus comprising:

(a) a stapling assembly that includes first, second, third, and fourth discrete staples and first and second rows of longitudinally extending staples, wherein each of the first, second, third, and fourth discrete staples includes a first leg, wherein the first and second rows of longitudinally extending staples include first and second legs; and (b) an anvil that together with the stapling assembly is configured to clamp tissue of a patient, the anvil comprising:

(i) a first staple forming pocket that is configured to sequentially transition the first legs of the first and second discrete staples from a non-deformed state to a deformed state with the same firing stroke, (ii) a second staple forming pocket that is configured to sequentially transition the first legs of the third and fourth discrete staples from a non-deformed state to a deformed state with the same firing stroke, (iii) a first row of longitudinally extending staple forming pocket pairs configured to sequentially transition first and second legs of the first row of longitudinally extending staples from a non-deformed state to a deformed state with the same firing stroke, and (iv) a second row of longitudinally extending staple forming pocket pairs configured to sequentially transition first and second legs of the second row of longitudinally extending staples from a non-deformed state to a deformed state with the same firing stroke, wherein the first, second, third, and fourth discrete staples are smaller than at least one of the first and second rows of longitudinally extending staples.

17. The apparatus of claim 16, wherein the first, second, third, and fourth discrete staples are arranged and configured to have a greater staple density in the deformed state than at least one of the first or second rows.

18. The apparatus of claim 16, wherein the first, second, third, and fourth discrete staples are smaller than both of the first and second rows of longitudinally extending staples.

19. The apparatus of claim 16, wherein the first, second, third, and fourth discrete staples are arranged and configured to have a greater staple density than both of the first and second rows of longitudinally extending staples.

20. The apparatus of claim 16, wherein the first, second, third, and fourth discrete staples are spaced apart in the non-deformed and deformed states, wherein the first and second rows of longitudinally extending staples are spaced apart in the non-deformed and deformed states.

* * * * *